United States Patent [19]

Findeisen et al.

[11] Patent Number: 4,988,718

[45] Date of Patent: Jan. 29, 1991

[54] PESTICIDAL SUBSTITUTED 4-HETEROCYCLYLOXIMINO-PYRAZOLIN-5-ONES, COMPOSITIONS AND USE

[75] Inventors: Kurt Findeisen, Odenthal; Klaus Jelich, Wuppertal; Gerd Hanssler, Leverkusen, all of Fed. Rep. of Germany

[73] Assignee: Bayer Aktiengesellschaft, Leverkusen, Fed. Rep. of Germany

[21] Appl. No.: 565,294

[22] Filed: Aug. 9, 1990

Related U.S. Application Data

[63] Continuation-in-part of Ser. No. 403,266, Sep. 5, 1989, Pat. No. 4,968,687.

[30] Foreign Application Priority Data

Sep. 15, 1988 [DE] Fed. Rep. of Germany ....... 3831430

[51] Int. Cl.⁵ ..................... A61K 43/56; A61K 43/82; C07D 403/12; C07D 417/12
[52] U.S. Cl. ..................................... 514/363; 514/364; 514/367; 514/369; 514/375; 514/376; 514/395; 514/397; 514/404; 548/132; 548/136; 548/167; 548/182; 548/221; 548/229; 548/327; 548/336; 548/364
[58] Field of Search ............... 548/132, 136, 167, 182, 548/221, 229, 327, 336, 364; 514/363, 364, 367, 369, 375, 376, 395, 397, 404

[56] References Cited

PUBLICATIONS

Jelich et al, *Chemical Abstracts,* vol. 106 (1987), No. 156,463w.

*Primary Examiner*—Robert W. Ramsuer
*Attorney, Agent, or Firm*—Sprung, Horn, Kramer & Woods

[57] ABSTRACT

Fungicidal substituted 4-heterocycloximinopyrazolin-5-ones of the formula

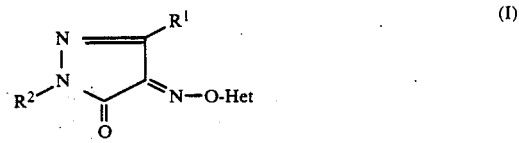

in which
R¹ and R² independently of one another in each case represent hydrogen, alkyl, alkenyl, alkinyl, cyanoalkyl, hydroxyalkyl, alkoxyalkyl, alkylthioalkyl, alkoxycarbonyl, hydroxycarbonylalkyl, alkoxycarbonylalkyl, aminocarbonylalkyl, alkylaminocarbonylalkyl or dialkylaminocarbonylalkyl, or represent in each case unsubstituted or in each case substituted oxiranylalkyl, aralkyl, heterocyclyl or aryl and
Het represents an unsubstituted or substituted heterocycle.

10 Claims, No Drawings

PESTICIDAL SUBSTITUTED 4-HETEROCYCLYLOXIMINO-PYRAZOLIN-5-ONES, COMPOSITIONS AND USE

This is a continuation-in-part of application Ser. No. 403,266, filed Sept. 5, 1989, now U.S. Pat. No. 4,968,687.

The invention relates to novel substituted 4-heterocyclyloximnio-pyrazolin-5-ones, several processes for their preparation and their use as pesticides.

It has been disclosed that certain substituted pyrazolinones, such as, for example, the compound 4-[(2,6-dihydroxypyrimidin-4-yl)-methoximino]-1,3-dimethyl-pyrazolin-5-one, possess fungicidal properties (cf. for example EP No. 213,360).

However, the effectiveness of these previously known compounds is not completely satisfactory in all fields of application, in particular at low application rates and concentrations.

Novel substituted 4-heterocycloximino-pyrazolin-5-ones of the general formula (I)

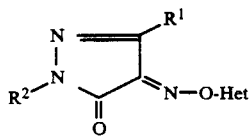

in which
$R^1$ and $R^2$ independently of one another in each case represent hydrogen, alkyl, alkenyl, alkinyl, cyanoalkyl, hydroxyalkyl, alkoxyalkyl, alkylthioalkyl, alkoxycarbonyl, hydroxycarbonylalkyl, alkoxycarbonylalkyl, aminocarbonylalkyl, alkaminocarbonylalkyl or dialkylaminocarbonylalkyl, or represent in each case unsubstituted or in each substituted oxiranylalkyl, aralkyl, heterocyclyl or aryl and
Het represents an unsubstituted or substituted heterocycle,
have been found.

The compounds of the formula (I) can be present as geometric isomers or isomer mixtures of various composition. Both the pure isomers and the isomer mixtures are claimed according to the invention.

Furthermore, it has been found that the novel substituted 4-heterocyclyloximino-pyrazoin-5-ones of the general formula (I)

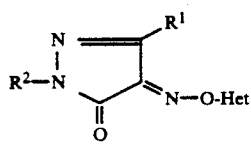

in which
$R^1$ and $R^2$ independently of one another in each case represent hydrogen, alkyl, alkenyl, alkinyl, cyanoalkyl, hydroxyalkyl, alkoxyalkyl, alkylthioalkyl, alkoxycarbonyl, hydroxycarbonylalkyl, alkoxycarbonylalkyl, aminocarbonylalkyl, alkylaminocarbonylalkyl or dialkylaminocarbonylalkyl, or represent in each case unsubstituted or in each case substituted oxiranylalkyl, aralkyl, heterocyclyl or aryl and
Het represents an unsubstituted or substituted heterocycle, are obtained when
(a) 4-oximino-pyrazolin-5-ones of the formula (II)

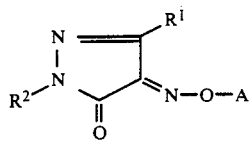

in which
$R^1$ and $R^2$ have the abovementioned meanings and
A represents hydrogen or an alkali metal cation,
are reacted with heterocycles of the formula (III)

$$\text{Het—E}^1 \quad (III)$$

in which
Het has the abovementioned meaning and
$E^1$ represents an electron-withdrawing leaving group,
if appropriate in the presence of a diluent, if appropriate in the presence of a reaction auxiliary and if appropriate in the presence of a catalyst, or when
(b) alkoximinocarboxylic acid esters of the formula (IV)

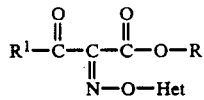

in which
R represents alkyl and
$R^1$ and Het have the abovementioned meanings,
are reacted with hydrazine derivatives of the formula (V)

$$R^2\text{—NH—NH}_2 \quad (V)$$

in which
$R^2$ has the abovementioned meaning,
if appropriate in the presence of a diluent, or when
(c) the 4-alkoximino-pyrazolin-5-ones, which can be obtained by process (a) or by process (b), of the formula (Ia)

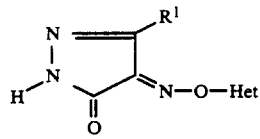

in which
$R^1$ and Het have the abovementioned meanings,
are reacted with alkylating agents of the formula (VI)

$$R^{2'}\text{—E}^2 \quad (VI)$$

in which
$R^{2'}$ represents alkyl, alkenyl, alkinyl, cyanoalkyl, hydroxyalkyl, alkoxyalkyl, alkylthioalkyl, hydroxycarbonylalkyl or alkoxycarbonylalkyl, or represents in each case unsubstituted or in each case substituted aralkyl or heterocyclyl, and
$E^2$ represents an electron-withdrawing leaving group, if appropriate in the presence of a diluent, if appropriate in the presence of an acid-binding agent and if appropriate in the presence of a catalyst.

Finally, it has been found that the novel substituted 4-heterocyclyoximino-pyrazolin-5-ones of the formula (I) possess a good effectiveness against pests.

Surprisingly, the novel substituted 4-heterocyclyoximino-pyrazolin-5-ones of the formula (I) show, inter alia, better fungicidal properties than the substituted pyrazolinones which are known from the prior art, and which are compounds of a similar chemical structure and type of action, such as, for example, the compound 4-[(2,6-dihydroxypyrimidin-4-yl)-methoximino]-1,3-dimethylpyrazolin-5-one.

Alkinyl in the general formulae denotes straight-chain branched alkyl, preferably having 1 to 8, particularly preferably having 1 to 4 and very particularly preferably having 1 to 3 carbon atoms. The following may be mentioned by way of example: methyl, ethyl, n- and i-propyl, n-, si, i- and ti-butyl, n-pentyl, i-pentyl, n-hexyl, i-hexyl, n-heptyl, i-heptyl, n-octyl and i-octyl.

Alkenyl in the general formulae denotes straight-chain or branched alkenyl, preferably having 2 to 8 and particularly preferably having 2 to 4 carbon atoms. The following may be mentioned by way of example and preferably: ethenyl, prop-1-enyl, prop-2-enyl, but-1-enyl, but-2-enyl and but-3-enyl.

Alinyl in the general formulae denotes straight-chain or branched alkinyl, preferably having 2 to 8 and particularly preferably having 3 or 4 carbon atoms. The following may be mentioned by way of example: ethinyl, prop-1-inyl, prop-2-inyl and but-3-inyl.

Cyanoalkyl in the general formulae denotes straight-chain or branched cyanoalkyl, preferably having 1 to 8 and particularly preferably having 1 or 2 carbon atoms in the alkyl moiety. The following may be mentioned by way of example: cyanomethyl, cyanoethyl, cyano-n-propyl, cyano-n-butyl and 2-cyano-t-butyl.

Hydroxyalkyl in the general formulae denotes straight-chain or branched hydroxyalkyl, preferably having 1 to 8, particularly preferably having 1 or 2 and very particularly preferably having 2 carbon atoms. The following may be mentioned by way of example: hydroxymethyl, hydroxyethyl, hydroxy-n-propyl, hydroxy-n-butyl and hydroxy-n-pentyl.

Alkoxyalkyl and alkylthioalkyl in the general formulae denote, in the various alkyl moieties, straight-chain or branched alkoxyalkyl and alkylthioalkyl, preferably having 1 to 8, particularly preferably having 1 or 2 and very particularly preferably having 1 carbon atom per alk.-moiety. The following may be mentioned by way of example: methoxymethyl, ethoxymethyl, n-propoxymethyl, i-propoxymethyl, i-propoxyethyl, n-butoxyethyl, methoxy-n-propyl, ethoxy-n-propyl, n-propoxy-n-propyl, i-propoxy-n-propyl, methoxy-n-butyl, methylthiomethyl, ethylthiomethyl, n-propylthiomethyl, i-propylthiomethy, n-butylthiomethyl, t-butylthiomethyl, methylthioethyl, ethylthioethyl, n-propylthioethyl, i-propylthioethyl, methylthio-n-propyl, ethylthio-n-propyl, n-propylthio-n-propyl, n-butylthio-n-propyl and t-butylthio-n-propyl.

Alkoxycarbonyl in the general formulae denotes straight-chain or branched alkoxycarbonyl, preferably having 1 to 8 and particularly preferably having 1 to 2 carbon atoms in the alkoxy moiety. The following may be mentioned by way of example: methoxycarbonyl, ethoxycarbonyl, n-propoxycarbonyl, i-butoxycarbonyl, t-butoxycarbonyl, i-butoxycarbonyl, n-pentoxycarbonyl, i-pentoxycarbonyl and n-hexoxycarbonyl.

Hydroxycarbonylalkyl and alkoxycarbonylalkyl in the general formulae represent hydroxycarbonylalkyl and alkoxycarbonylalkyl which are straight-chain or branched in the alkyl and alkoxy moiety, preferably having 1 to 8 and particularly preferably having 1 or 2 carbon atoms per alkyl radical. The following may be mentioned by way of example: hydroxycarbonylmethyl, hydroxycarbonylethyl, hydroxycarbonyl-n-propyl, hydroxycarbonyl-i-propyl, hydroxycarbonyl-n-butyl, methoxycarbonylmethyl, ethoxycarbonylmethyl, n-propoxycarbonylmethyl, i-propoxycarbonylmethyl, n-butoxycarbonylmethyl, t-butoxycarbonylmethyl, ethoxycarbonylethyl, n-propoxycarbonylethyl, i-propoxycarbonylethyl, i-propoxycarbonylethyl, n-butoxycarbonylethyl, t-butoxycarbonylethyl, methoxycarbonyl-n-propyl, ethoxycarbonyl-n-propyl, n-propoxycarbonyl-n-propyl and t-butoxycarbonyl-n-propyl.

Aminocarbonylalkyl, alkylaminocarbonylalkyl and dialkylaminocarbonylalkyl in the general formulae represent the radicals indicated, where the alkyl radicals are straight-chain or branched and each radical having preferably 1 to 8, particularly preferably 1 to 2, carbon atoms. The following may be mentioned by way of example: aminocarbonylmethyl, aminocarbonylethyl, aminocarbonyl-n-propyl, aminocarbony-i-propyl, aminocarbonyl-n-butyl, aminocarbonyl-n-pentyl, methylaminocarbonylmethyl, ethylaminocarbonylmethyl,n-propylaminocarbonylmethyl,i-propylaminocarbonylmethyl, n-butylaminocarbonylmethyl, methylaminocarbonylethyl, ethylaminocarbonylethyl, n-propylaminocarbonylethyl, i-propylaminocarbonylethyl, n-butylaminocarbonylethyl, methylaminocarbonyl-n-propyl, ethylaminocarbonyl-n-propyl, n-propylaminocarbonyl-n-propyl, t-butylaminocarbonyl-n-propyl, dimethylaminocarbonylmethyl, diethylaminocarbonylmethyl, di-n-propylaminocarbonylmethyl, dimethylaminocarbonylethyl, diethylaminocarbonylethyl, di-n-propylaminocarbonylethyl, dimethylaminocarbonyl-n-propyl, diethylaminocarbonyl-n-propyl and diethylaminocarbonyl-n-butyl.

Oxiranylalkyl in the general formulae denotes an oxiranyl ring bonded via a straight-chain or branched alkyl radical, preferably having 1 to 4, particularly preferably having 1 or 2, carbon atoms. The following may be mentioned by way of example: oxiranylmethyl, oxiranylethyl, oxiranyl-n-propyl and oxiranyl-n-butyl.

Aralkyl in the general formula denotes an aralkyl radical which is straight-chain or branched in the alkyl moiety and which has preferably 6 to 10 and particularly preferably 6 carbon atoms in the aryl radial and 1 to 4, particularly preferably 1 or 2, carbon atoms in the alkyl radical. The acyl radical denotes naphthyl or phenyl, preferably phenyl.

Aryl has the meaning mentioned above in the general formulae.

Heterocyclyl in the general formulae in the definitions of $R^1$ and $R^2$ denotes a saturated or unsaturated radical having 5 to 7 ring members, preferably having 5 ring members, and 1 to 3, preferably 1, heteroatom, such as nitrogen, oxygen or sulphur, or the sulphonyl group, preferably sulphur or sulphonyl. The following may be mentioned by way of example: thienyl, tetrahydrothienyl and 1,1-dioxotetrahydrothienyl.

Het in the general formulae represents a saturated or unsaturated ring having 5 to 7, preferably 5 or 6, ring members, of which 1 to 4, preferably 1 to 3, ring member are identical or different heteroatoms. Heteroatoms or heterogroups which may be mentioned are: nitrogen, oxygen, sulphur, sulphinyl and sulphonyl, preferably nitrogen, oxygen, sulphur and sulphonyl. The heterocycles can also be benzo-fused. The following may be mentioned by way of example: pyrrole, oxazole, imidazole, thiazole, thiadiazole, pyrazole, pyridine, pyrimidine, triazine, pyridazine, oxolane, thiolane, thiophene, indole, benzofuran, benzoxazole and benzimidazole, particularly preferably pyrimidine, thiadizole and triazine.

Aryl, heterocyclyl and aralkyl in the general formulae can be monosubstituted to polysubstitubed, preferably monosubstituted to pentasubstituted, particularly preferably monosubstituted to trisubstituted, in the rings by identical or different substituents.

Substituents in the aryl radicals as such or in the compositions, such as aralkyl, which may be mentioned are: halogen, such as fluorine, chlorine, bromine and iodine, very particularly preferably chlorine; cyano, nitro, hydroxyl, straight-chain or branched alkyl, alkoxy, dioxyalkylene, alkylcarbonyloxy and alkylthio, preferably having up to 4 carbon atoms per radical, particularly preferably having 1 to 2 carbon atoms, straight-chain or branched halogenoalkyl, halogenoalkoxy and halogenoalkylthio, preferably having 1 to 4 carbon atoms and 1 to 3 identical or different halogen atoms, such as fluorine, chlorine, bromine and iodine, particularly preferably having 1 or 2 carbon atoms and 1 to 3 identical or different halogen atoms, such as fluorine and chlorine, and furthermore phenyl.

Substituents for the het radicals in the general formulae which may be mentioned are: hydroxyl, halogen, preferably fluorine, chlorine, bromine and iodine, particularly preferably fluorine, chlorine and bromine, cyano, nitro, amino, straight-chain or branched alkyl, alkoxy and alkylthio, preferably having 1 to 4 carbon atoms in each case, particularly preferably alkyl having 1 to 4, or alkoxy and alkylthio having 1 to 2, carbon atoms, straight-chain or branched halogenoalkyl, halogenoalkoxy and halogenoalkylthio, preferably having 1 to 4 carbon atoms in each case and 1 to 9 identical or different halogen atoms, such as fluorine, chlorine, bromine and iodine, particularly preferably having 1 or 2 carbon atoms and 1 to 3 identical or different halogen atoms, such as fluorine and chlorine, straight-chain or branched alkylamino, dialkylamino, alkoxycarbonyl and alkoximinoalkyl, preferably having 1 to 4 carbon atoms per alkyl radical, particularly preferably having 1 or 2 carbon atoms per alkyl radical, furthermore phenyl or phenyl which is preferably monosubstituted to pentasubstituted, particularly preferably monosubstituted to trisubstituted, by identical or different substituents from the series comprising nitro, halogen, such as fluorine, chlorine, bromine and iodine, particularly preferably chlorine, or straight-chain or branched alkyl or alkoxy preferably 1 to 4, particularly preferably 1 or 2, carbon atoms.

Formula (I) provides a general definition of the substituted 4-heterocyclyloximino-pyrazolin-5-ones according to the invention. Preferred compounds of the formula (I) are those in which $R^1$ and $R^2$ independently of one another in each case represent hydrogen, in each case represent straight-chain or branched alkyl, alkenyl, alkinyl, cyanoalkyl, hydroxyalkyl, alkoxyalkyl, alkylthioalkyl, alkoxycarbonyl, hydroxycarbonylalkyl, alkoxycarbonylalkyl, aminocarbonylalkyl, alkylaminocarbonylalkyl or dialkylaminocarbonylalkyl, in each case having up to 8 carbon atoms in the individual alkyl or alkenyl or alkinyl moieties, or represent oxiranylalkyl having 1 to 4 carbon atoms in the straight-chain or branched alkyl moiety, or represent 1,1-dioxotetrahydrothienyl, or represent aralkyl which has 1 to 4 carbon atoms in the straight-chain or branched alkyl moiety and 6 to 10 carbon atoms in the aryl moiety and which is unsubstituted or monosubstituted to polysubstituted by identical or different substituents, or represent aryl which has 6 to 10 carbon atoms and which is unsubstituted or monosubstituted to polysubstituted by identical or different substituents, suitable substituents in the aryl moieties in each case being: halogen, cyano, nitro, hydroxyl, in each case straight-chain or branched alkyl, alkoxy, dioxyalkylene, alkylcarbonyloxy and alkylthio, in each case having up to 4 carbon atoms, in each case straight-chain or branched halogenoalkyl, halogenoalkoxy or halogenoalkylthio, in each case having 1 to 4 carbon atoms and 1 to 9 identical or different halogen atoms, or phenyl and Het represents a saturated or unsaturated five-membered or six-membered heterocycle which has 1 to 3 identical or different hetero atoms or hetero groupings, in particularly nitrogen, oxygen, sulphur, sulphinyl or sulphonyl, and which is substituted or monosubstituted to polysubstituted by identical or different substituents, and/or which is benzo-fused, suitable substituents being: hydroxyl, halogen, cyano, nitro, amino, in each case straight-chain or branched alkyl, alkoxy or alkylthio, in each case having 1 to 4 carbon atoms, in each case straight-chain or branched halogenoalkyl, halogenoalkoxy or halogenoalkylthio, in each case having 1 to 4 carbon atoms and 1 to 9 identical or different halogen atoms, in each case straight-chain or branched alkylamino, dialkylamino, alkoxycarbonyl or alkoximinoalkyl, in each case having 1 to 4 carbon atoms in the individual alkyl moieties, or phenyl which is unsubstituted or monosubstituted to polysubstituted by identical or different substituents from the series comprising nitro, halogen and/or in each case straight-chain or branched alkyl or alkoxy, in each case having 1 to 4 carbon atoms.

Particularly preferred compounds of the formula (I) are those in which $R^1$ and $R^2$ independently of one another in each case represent hydrogen, methyl, ethyl, n- or i-propyl, n-, i-, s- or ti-butyl, allyl, butenyl, propargyl, cyanomethyl, cyanoethyl, hydroxymethyl, hydroxyethyl, methoxymethyl, methoxyethyl, ethoxymethyl, ethoxyethyl, methylthomethyl, methoxycarbonyl, ethoxycarbonyl, hydroxycarbonylmethyl, hydroxycarbonylethyl, methoxycarbonylmethyl, methoxycarbonylethyl, ethoxycarbonylmethyl, ethoxycarbonylethyl, aminocarbonylmethyl, methylaminocarbonylmethyl, ethylaminocarbonylmethyl, dimethylaminocarbonylmethyl, diethylaminocarbonylmethyl, aminocarbonylethyl, oxiranylmethyl, oxiranylethyl, or represent 1,1-dioxotetrahydrothien-3-yl, or represent phenyl or benzyl which are unsubstituted or in each case monosubstituted to trisubstituted by identical or different substituents, suitable phenyl substituents in each case being: fluorine, chlorine, bromine, iodine, cyano, nitro, hydroxyl, methyl, ethyl, n- or i-propyl, n-, i-, si or t-butyl, methoxy, ethoxy, dioxymethylene, dioxyethylene, methylthio, ethylthio, acetoxy or propionyloxy, chloromethyl, dichloromethyl, trichloromethyl, trifluoromethyl, dichlorofluoromethyl, chlorodifluoromethyl, trifluoromethoxy, trifluoromethylthio or phenyl, and Het represents a heterocycle which is bonded via a carbon atom, of the formula

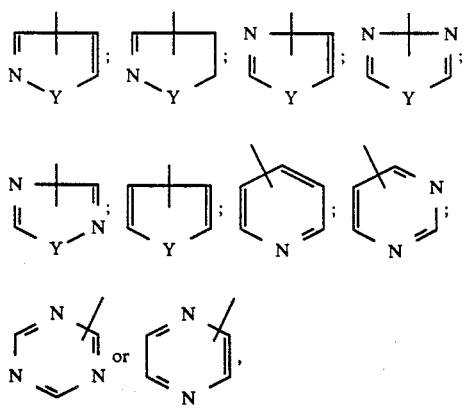

and which is unsubstituted or monosubstituted to trisubstituted by identical or different substituents, and/or benzo-fused, suitable substituents in each case being: hydroxyl, amino, cyano, nitro, fluorine, chlorine, bromine, methyl, ethyl, n- or i-propyl, n-, i- s- or t-butyl, methoxy, ethoxy, methylthio, ethylthio, trifluoromethyl, trichloromethyl, dichloromethyl, chloromethyl, difluoromethyl, fluoromethyl, trifluoromethoxy, difluoromethoxy, trifluoromethylthio, methylamino, ethylamino, dimethylamino, dimethylamino, methoxycarbonyl, ethoxycarbonyl, methoximinomethyl ethoximinomethyl, methoximinoethyl or ethoximinoethyl, or phenyl which is unsubstituted or monosubstituted to trisubstituted by identical or different substituents from the series comprising chlorine, nitro, methyl, ethyl and/or methoxy, and where Y in each case represents oxygen, sulphur, sulphinyl or sulphonyl.

Very particularly preferred compounds of the formula (I) are those in which $R^1$ and $R^2$ independently of one another in each case represent hydrogen, methyl, ethyl, n- or i-propyl, or represent methoxymethyl, or represent hydroxyethyl, or represent methoxycarbonyl or ethoxycarbonyl, or represent phenyl which is unsubstituted or monosubstituted or disubstituted by identical or different substituents from the series comprising chlorine, nitro, methyl, ethyl and/or methoxy, and Het represents a heterocycle of the formula

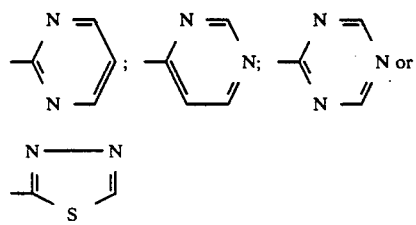

which is unsubstituted or monosubstituted to trisubstituted by identical or different substituents, suitable substituents in each case being: hydroxyl, amino, cyano, nitro, fluorine, chlorine, bromine, methyl, ethyl, methoxy, ethoxy, methylthio, ethylthio, trifluoromethyl, trichloromethyl, dichloromethyl, chloromethyl, methylamino, ethylamino, dimethylamino, diethylamino, or phenyl which is unsubstituted or monosubstituted or disubstituted by identical or different substituents from the series comprising chlorine, nitro, methyl, ethyl and/or methoxy.

In addition to the compounds mentioned in the Preparation Examples, the following substituted 4-heterocyclyloximino-pyrazolin-5-ones of the general formula (I) may be mentioned individually:

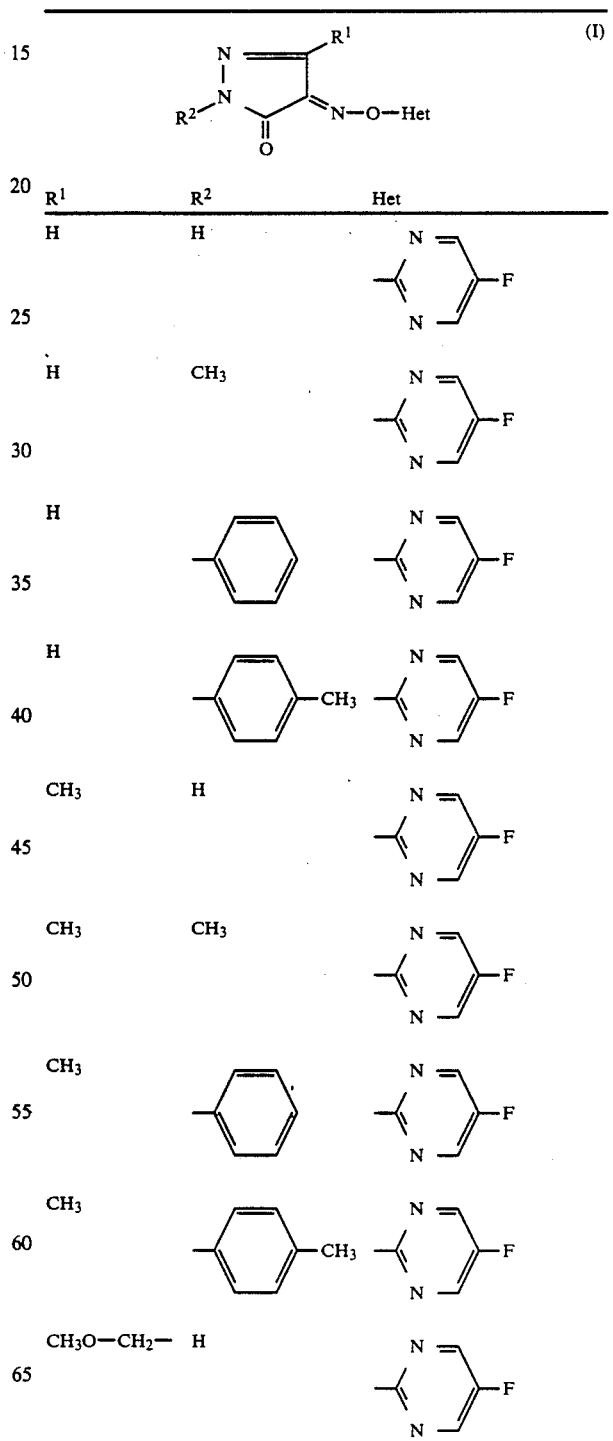

-continued

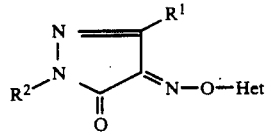

| R¹ | R² | Het |
|---|---|---|
| CH₃O—CH₂— | CH₃ | 5-F pyrimidin-2-yl |
| CH₃O—CH₂— | phenyl | 5-F pyrimidin-2-yl |
| CH₃O—CH₂— | p-tolyl | 5-F pyrimidin-2-yl |
| phenyl | H | 5-F pyrimidin-2-yl |
| phenyl | CH₃ | 5-F pyrimidin-2-yl |
| phenyl | phenyl | 5-F pyrimidin-2-yl |
| phenyl | p-tolyl | 5-F pyrimidin-2-yl |
| H | H | 5-CF₃ pyrimidin-2-yl |
| H | CH₃ | 5-CF₃ pyrimidin-2-yl |
| H | phenyl | 5-CF₃ pyrimidin-2-yl |
| H | p-tolyl | 5-CF₃ pyrimidin-2-yl |
| CH₃ | H | 5-CF₃ pyrimidin-2-yl |
| CH₃ | CH₃ | 5-CF₃ pyrimidin-2-yl |
| CH₃ | phenyl | 5-CF₃ pyrimidin-2-yl |
| CH₃ | p-tolyl | 5-CF₃ pyrimidin-2-yl |
| CH₃O—CH₂— | H | 5-CF₃ pyrimidin-2-yl |
| CH₃O—CH₂— | H | 5-CF₃ pyrimidin-2-yl |
| CH₃O—CH₂— | CH₃ | 5-CF₃ pyrimidin-2-yl |
| CH₃O—CH₂— | phenyl | 5-CF₃ pyrimidin-2-yl |
| CH₃O—CH₂— | p-tolyl | 5-CF₃ pyrimidin-2-yl |
| phenyl | H | 5-CF₃ pyrimidin-2-yl |
| phenyl | CH₃ | 5-CF₃ pyrimidin-2-yl |

-continued
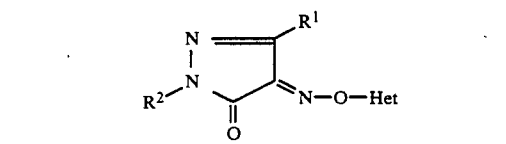
| R¹ | R² | Het |
|---|---|---|
| 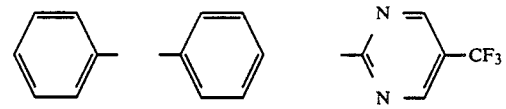 | | |
| 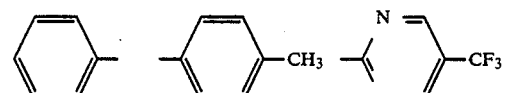 | | |
| H | H | 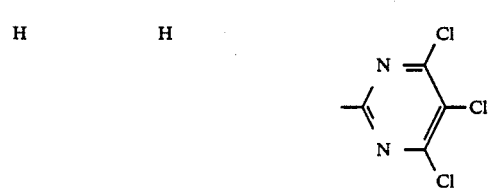 |
| H | CH₃ | 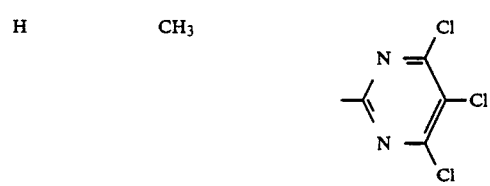 |
| H | 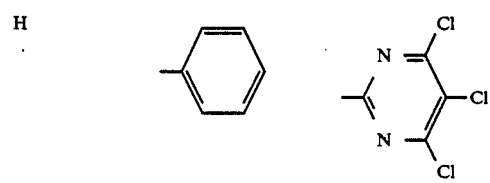 | |
| H | 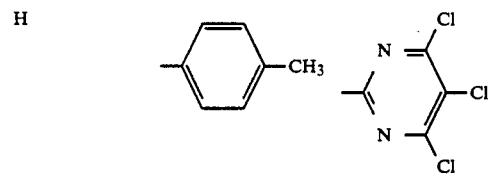 | |
| CH₃ | H |  |
| CH₃ | CH₃ | 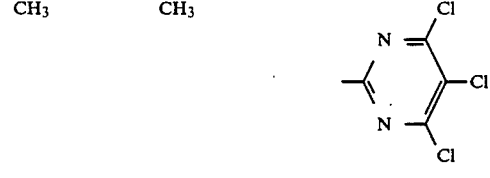 |
-continued
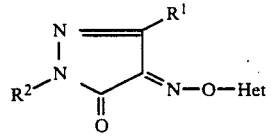
| R¹ | R² | Het |
|---|---|---|
| CH₃ | 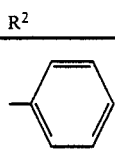 | 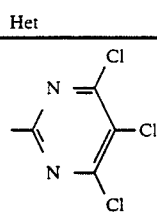 |
| CH₃ |  | 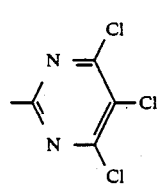 |
| CH₃O—CH₂— | H | 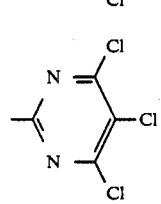 |
| | CH₃O—CH₂— CH₃ |  |
| CH₃O—CH₂— | 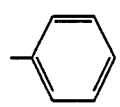 | 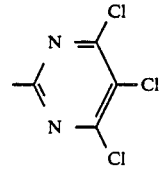 |
| CH₃O—CH₂— | 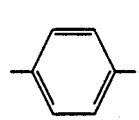 | 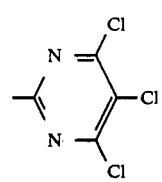 |
| 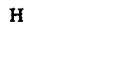 | H | 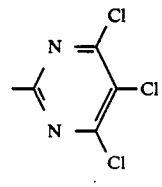 |
| 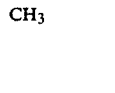 | CH₃ | 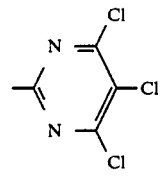 |

-continued $$\text{(I)}$$

Structure: pyrazolone with substituents R¹ at position adjacent to =N-, R² on N, and =N-O-Het group.

| R¹ | R² | Het |
|---|---|---|
| phenyl | phenyl | 2,5,6-trichloropyrimidin-4-yl |
| phenyl | 4-methylphenyl | 2,5,6-trichloropyrimidin-4-yl |
| H | H | 2,5,6-trichloropyrimidin-4-yl |
| H | CH₃ | 2,5,6-trichloropyrimidin-4-yl |
| H | phenyl | 2,5,6-trichloropyrimidin-4-yl |
| H | 4-methylphenyl | 2,5,6-trichloropyrimidin-4-yl |
| CH₃ | H | 2,5,6-trichloropyrimidin-4-yl |
| CH₃ | CH₃ | 2,5,6-trichloropyrimidin-4-yl |
| CH₃ | phenyl | 2,5,6-trichloropyrimidin-4-yl |
| CH₃ | 4-methylphenyl | 2,5,6-trichloropyrimidin-4-yl |
| CH₃O—CH₂— | H | 2,5,6-trichloropyrimidin-4-yl |
| CH₃O—CH₂— | CH₃ | 2,5,6-trichloropyrimidin-4-yl |
| CH₃O—CH₂— | phenyl | 2,5,6-trichloropyrimidin-4-yl |
| CH₃O—CH₂— | 4-methylphenyl | 2,5,6-trichloropyrimidin-4-yl |
| phenyl | H | 2,5,6-trichloropyrimidin-4-yl |
| phenyl | CH₃ | 2,5,6-trichloropyrimidin-4-yl |

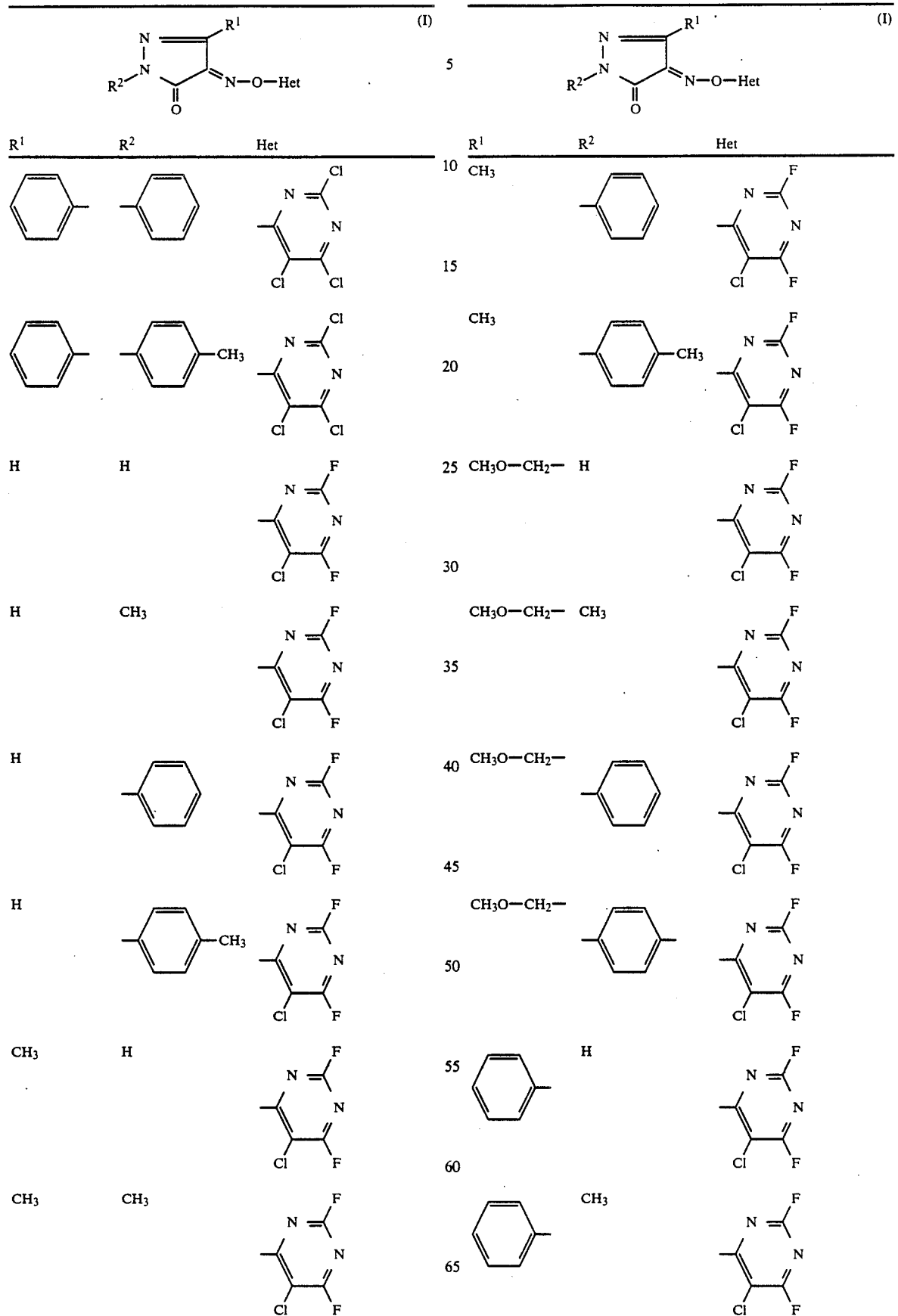

-continued $$\text{(I)}$$

Structure (I): pyrazole ring with R¹ at 4-position, R² on N, =N-O-Het oxime, and ketone.

| R¹ | R² | Het |
|---|---|---|
| C₆H₅ | C₆H₅ | 2-F, 5-Cl, 6-F pyrimidin-4-yl |
| C₆H₅ | 4-CH₃-C₆H₄ | 2-F, 5-Cl, 6-F pyrimidin-4-yl |
| H | H | 2-F, 5-Cl, 6-Cl pyrimidin-4-yl |
| H | CH₃ | 2-F, 5-Cl, 6-Cl pyrimidin-4-yl |
| H | C₆H₅ | 2-F, 5-Cl, 6-Cl pyrimidin-4-yl |
| H | 4-CH₃-C₆H₄ | 2-F, 5-Cl, 6-Cl pyrimidin-4-yl |
| CH₃ | H | 2-F, 5-Cl, 6-Cl pyrimidin-4-yl |
| CH₃ | CH₃ | 2-F, 5-Cl, 6-Cl pyrimidin-4-yl |
| CH₃ | C₆H₅ | 2-F, 5-Cl, 6-Cl pyrimidin-4-yl |
| CH₃ | 4-CH₃-C₆H₄ | 2-F, 5-Cl, 6-Cl pyrimidin-4-yl |
| CH₃O—CH₂— | H | 2-F, 5-Cl, 6-Cl pyrimidin-4-yl |
| CH₃O—CH₂— | CH₃ | 2-F, 5-Cl, 6-Cl pyrimidin-4-yl |
| CH₃O—CH₂— | C₆H₅ | 2-F, 5-Cl, 6-Cl pyrimidin-4-yl |
| CH₃O—CH₂— | 4-CH₃-C₆H₄ | 2-F, 5-Cl, 6-Cl pyrimidin-4-yl |
| C₆H₅ | H | 2-F, 5-Cl, 6-Cl pyrimidin-4-yl |
| C₆H₅ | CH₃ | 2-F, 5-Cl, 6-Cl pyrimidin-4-yl |

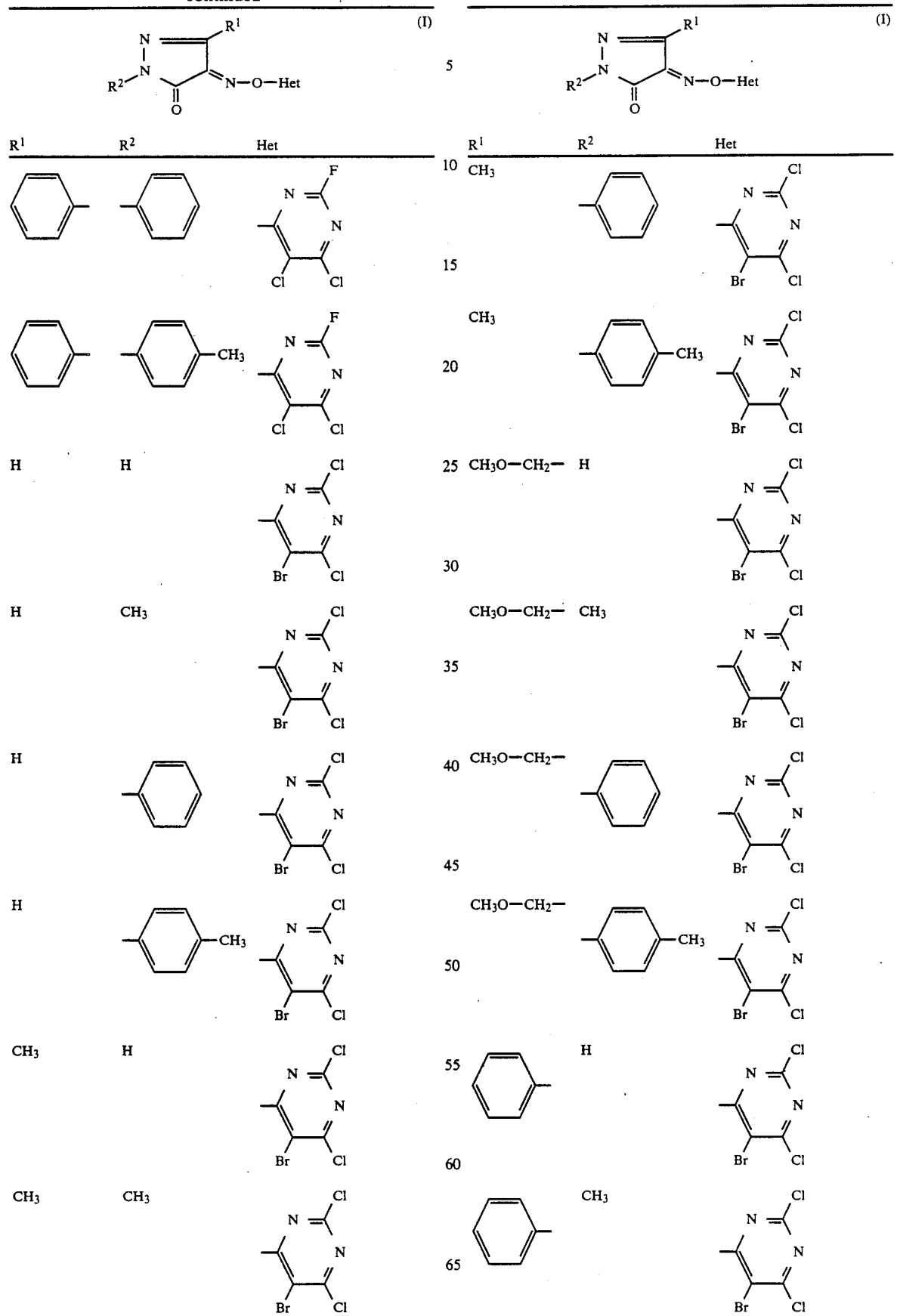

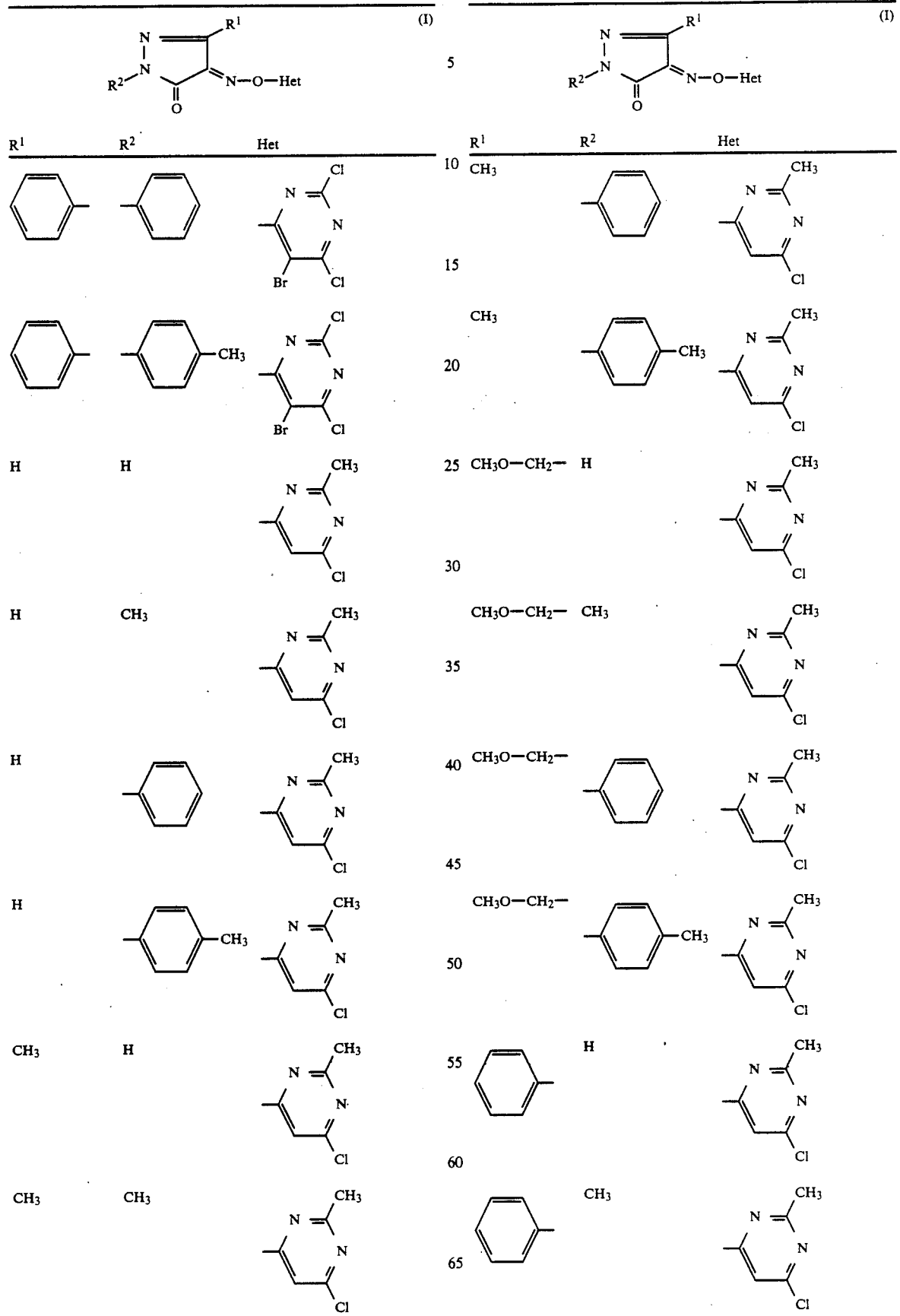

-continued
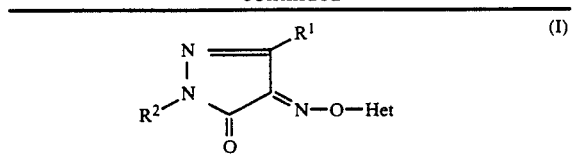
| R¹ | R² | Het |
|---|---|---|
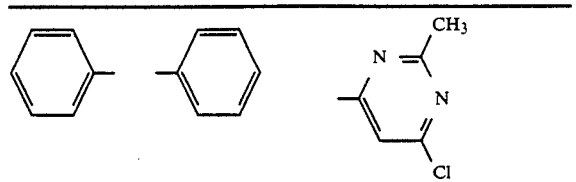
-continued
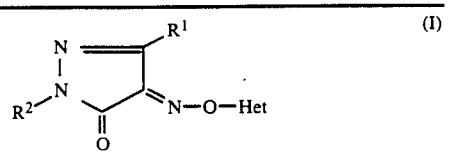
| R¹ | R² | Het |
|---|---|---|
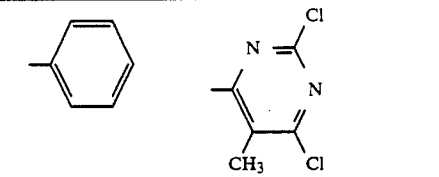

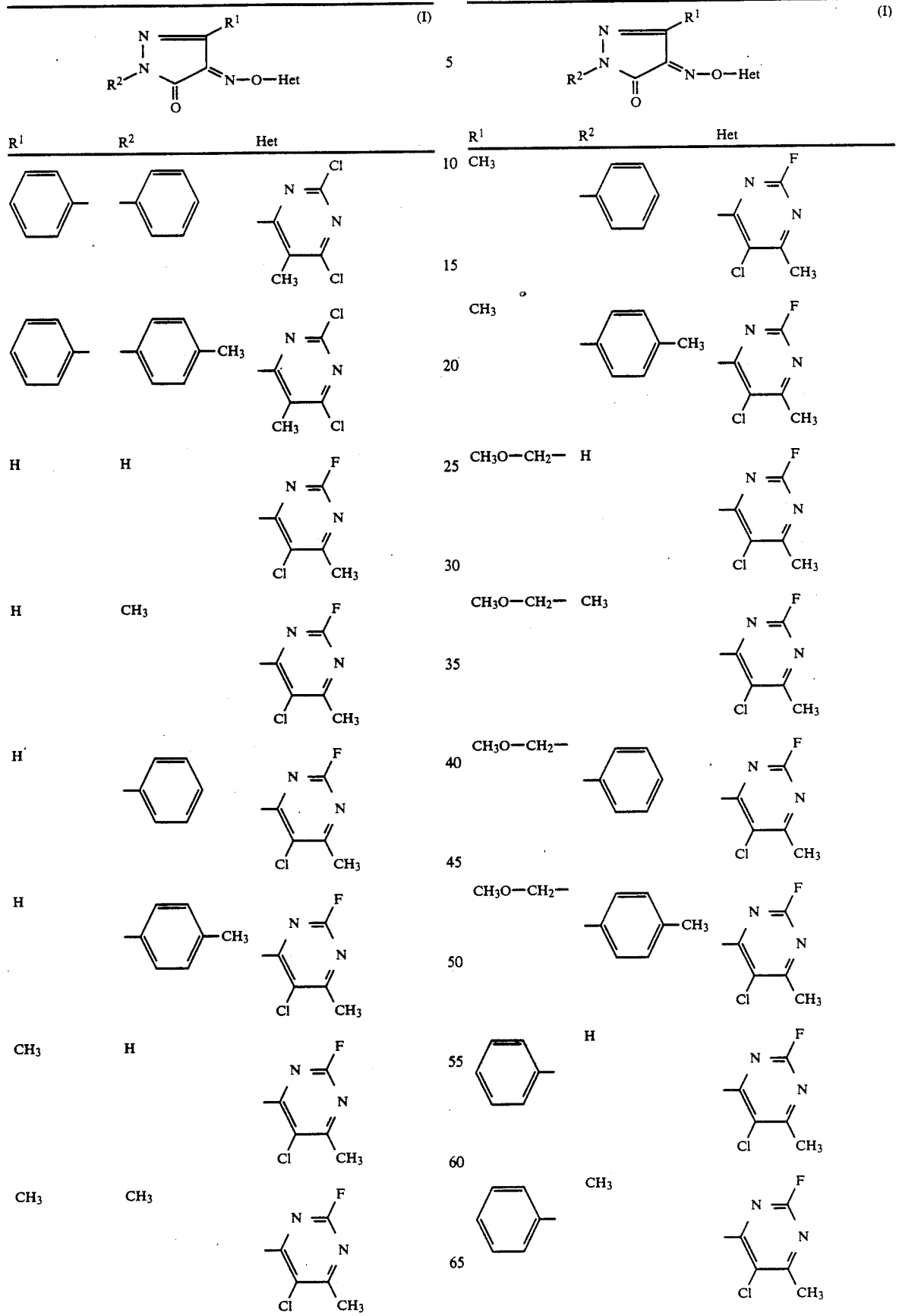

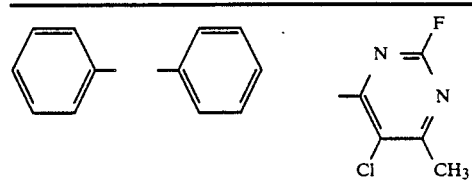
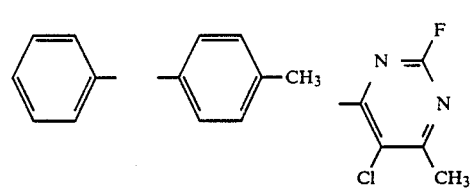
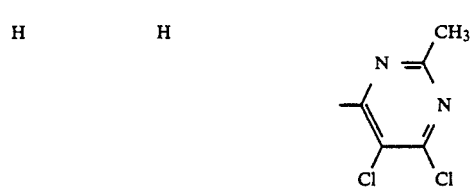
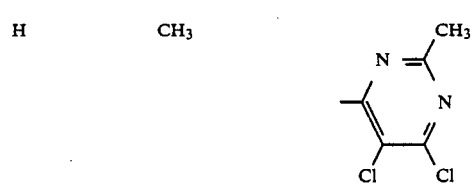
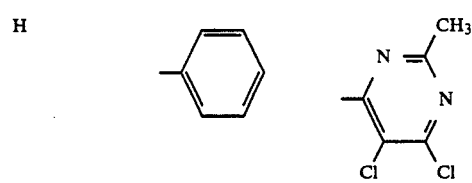
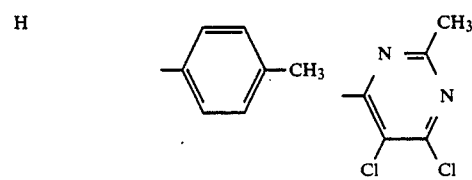
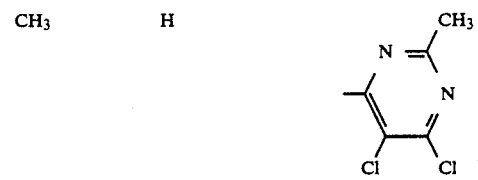
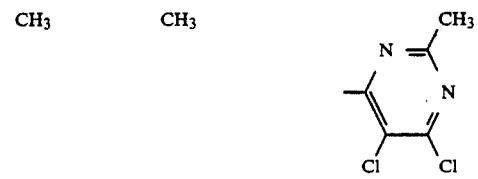
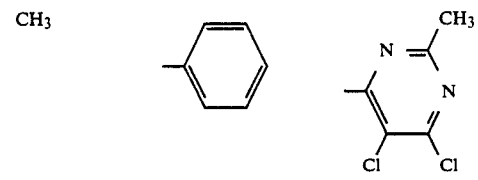
-continued
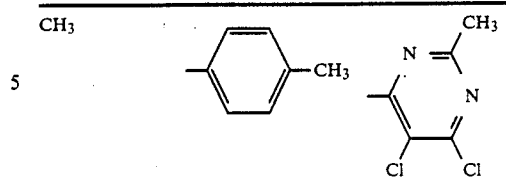
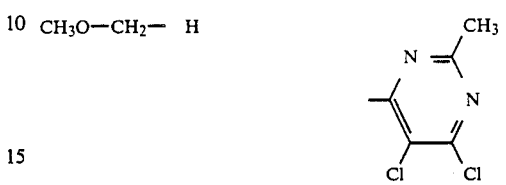
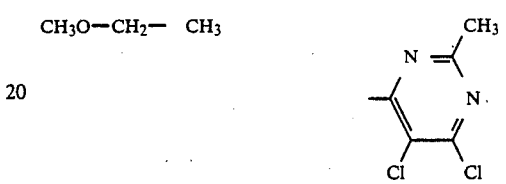
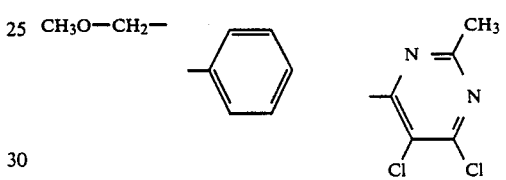
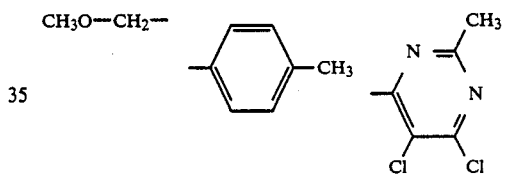
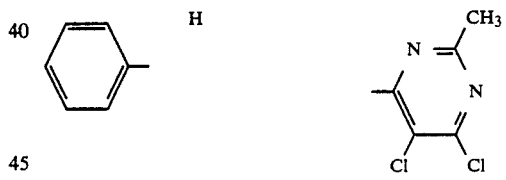
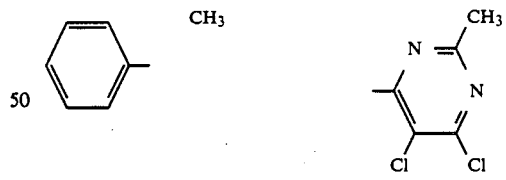
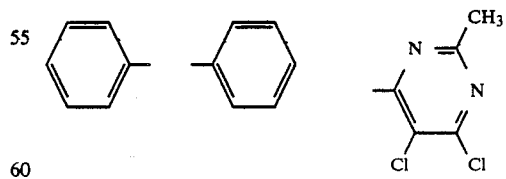
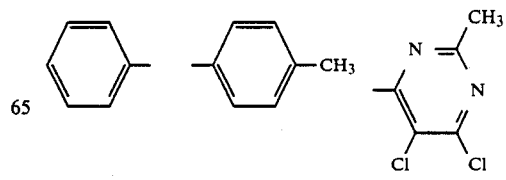

| | | |
|---|---|---|
| H | H | 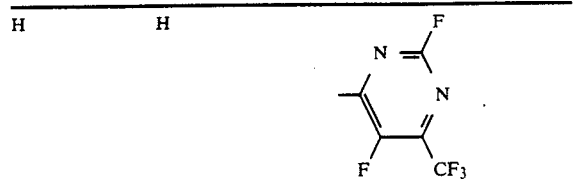 |
| H | CH₃ | 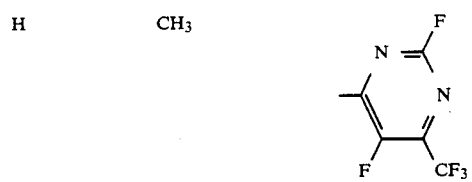 |
| H | phenyl | 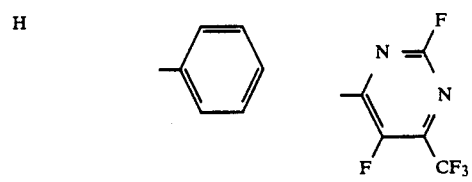 |
| H | p-tolyl | 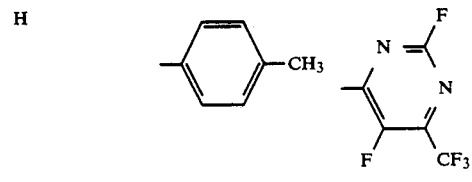 |
| CH₃ | H |  |
| CH₃ | CH₃ | |
| CH₃ | phenyl | 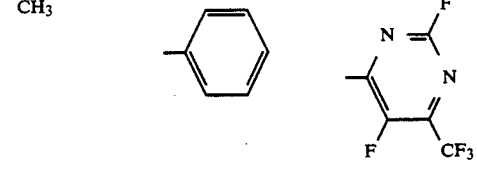 |
| CH₃ | p-tolyl | 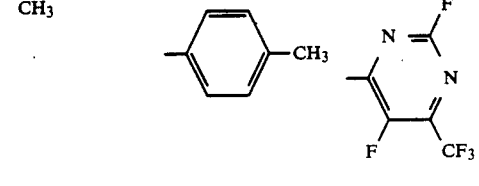 |
| CH₃O—CH₂— | H |  |
| | | |
|---|---|---|
| CH₃O—CH₂— | CH₃ | 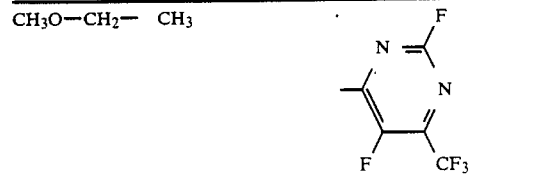 |
| CH₃O—CH₂— | phenyl | 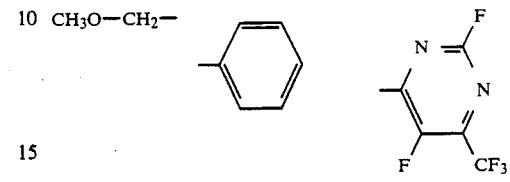 |
| CH₃O—CH₂— | p-tolyl | 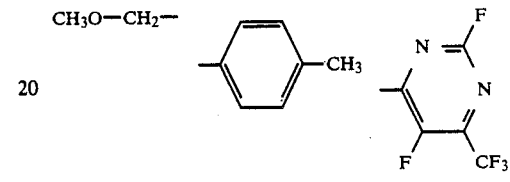 |
| phenyl | H |  |
| phenyl | CH₃ | 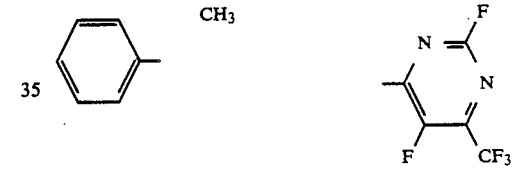 |
| phenyl | phenyl | 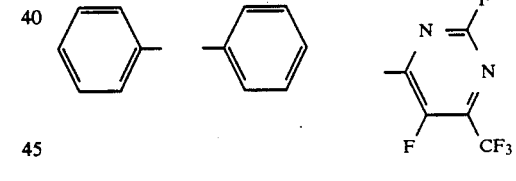 |
| phenyl | p-tolyl | 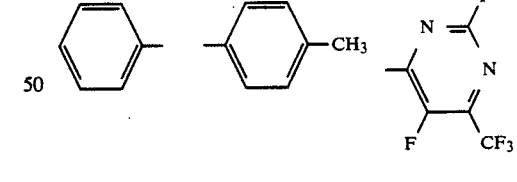 |
| H | H | 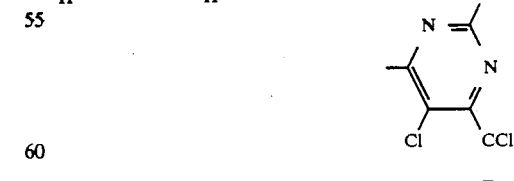 |
| H | CH₃ | 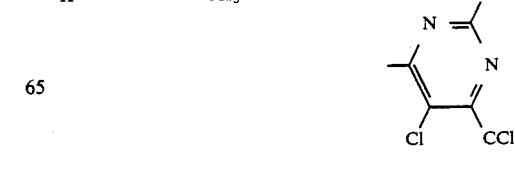 |

| | | |
|---|---|---|
| H | 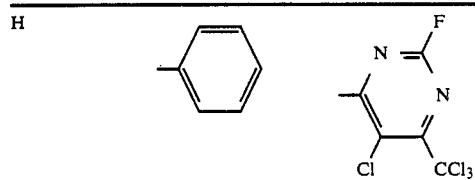 | |
| H | 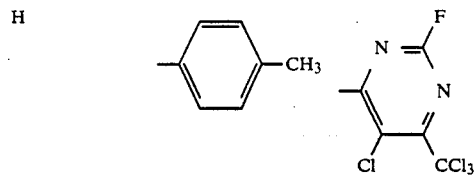 | |
| CH₃ | H | 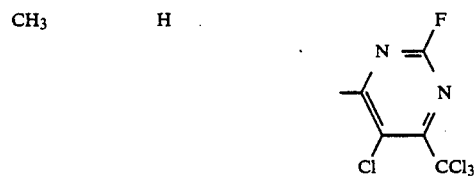 |
| CH₃ | CH₃ | 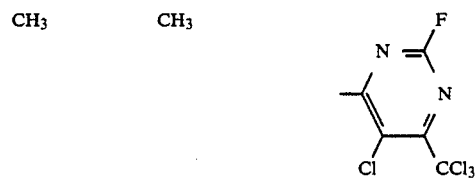 |
| CH₃ | 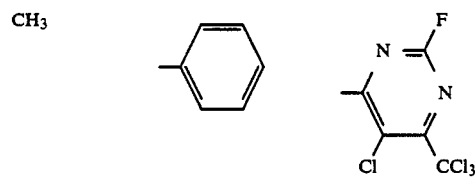 | |
| CH₃ | 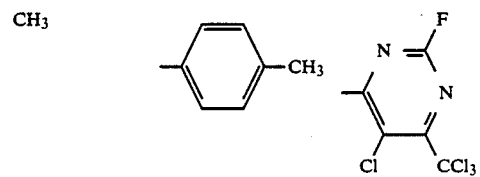 | |
| CH₃O—CH₂— | H | 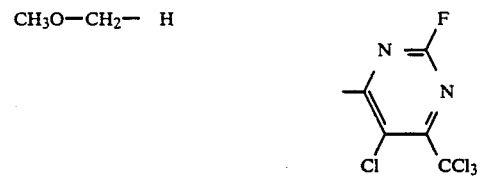 |
| CH₃O—CH₂— | CH₃ | 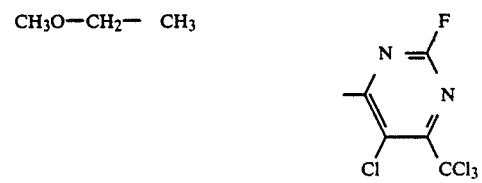 |
| CH₃O—CH₂— | 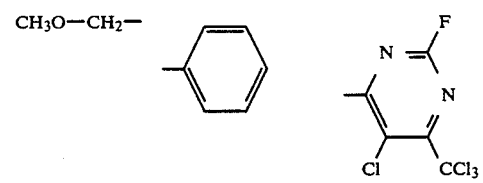 | |
| | | |
|---|---|---|
| CH₃O—CH₂— | 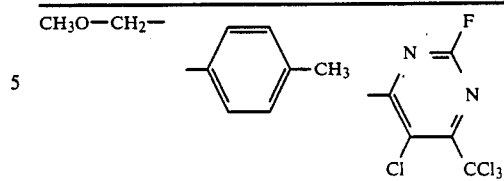 | |
| H | 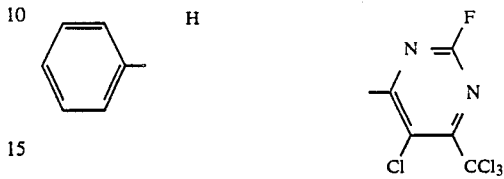 | |
| CH₃ | 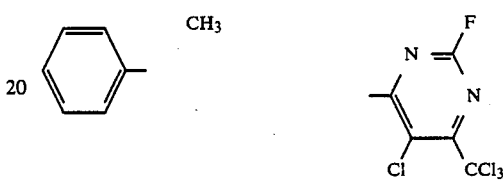 | |
| 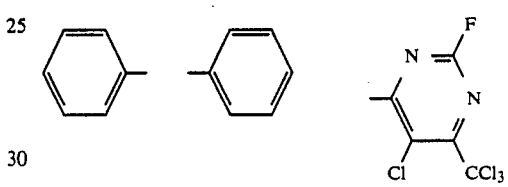 | | |
| 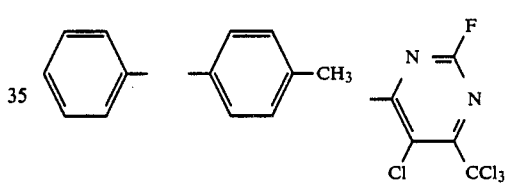 | | |
| H | H | 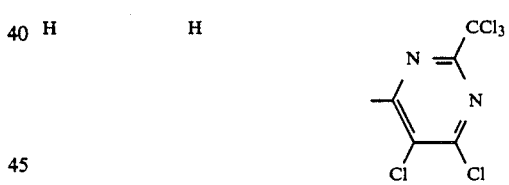 |
| H | CH₃ | 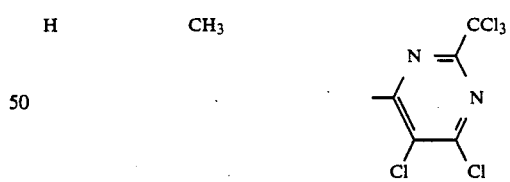 |
| H | 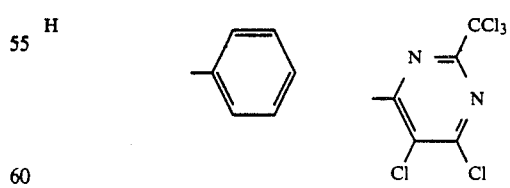 | |
| H | 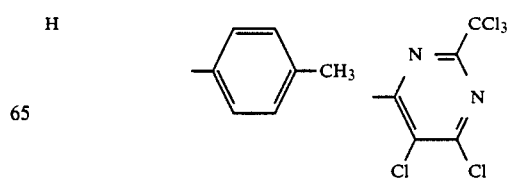 | |

-continued
| | | |
|---|---|---|
| CH₃ | H | 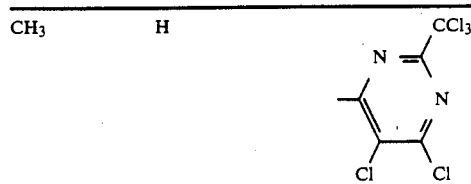 |
| CH₃ | CH₃ | 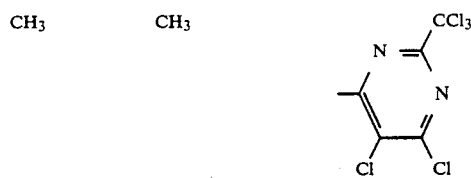 |
| CH₃ | 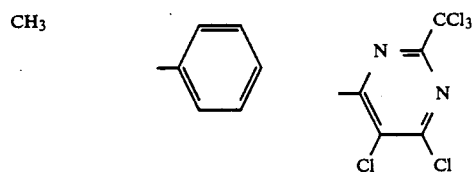 (phenyl) | |
| CH₃ | 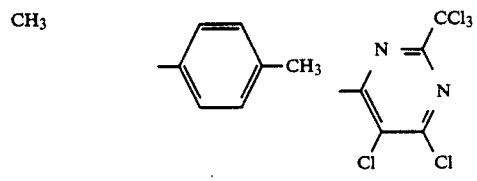 (p-tolyl) | |
| CH₃O—CH₂— | H |  |
| CH₃O—CH₂— | CH₃ | 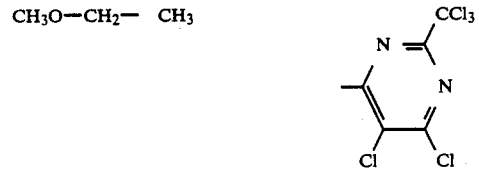 |
| CH₃O—CH₂— | 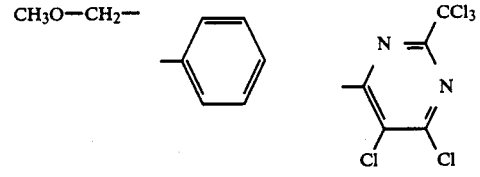 (phenyl) | |
| CH₃O—CH₂— | 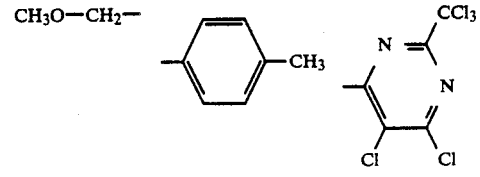 (p-tolyl) | |
| 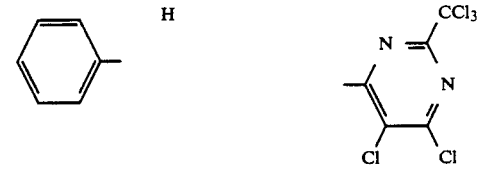 (phenyl) | H | |
-continued
| | | |
|---|---|---|
| phenyl | CH₃ | 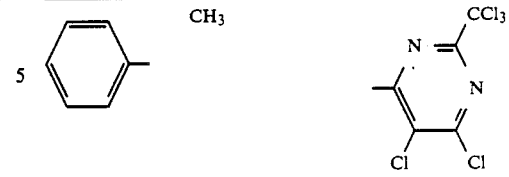 |
| phenyl | phenyl | 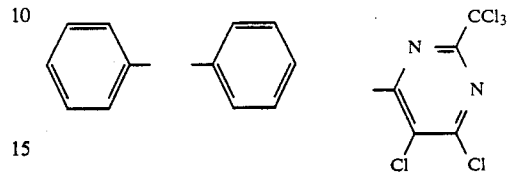 |
| phenyl | p-tolyl | 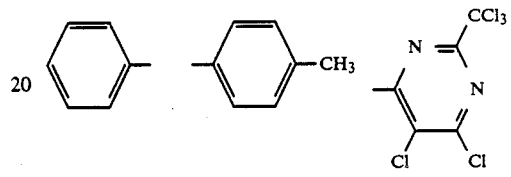 |
| H | H | 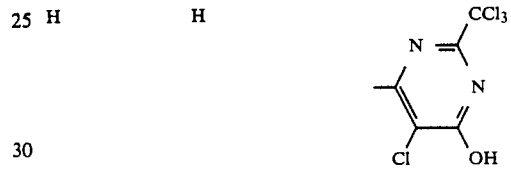 |
| H | CH₃ | 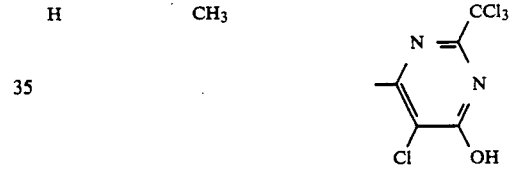 |
| H | phenyl | 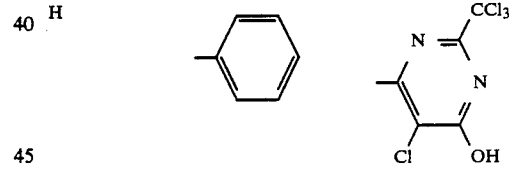 |
| H | p-tolyl | 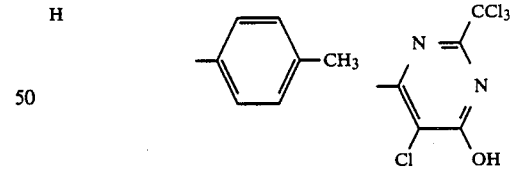 |
| CH₃ | H | 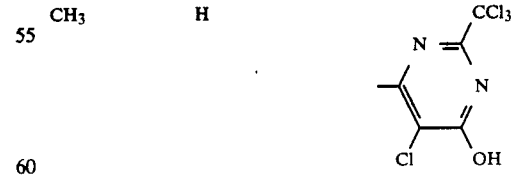 |
| CH₃ | CH₃ | 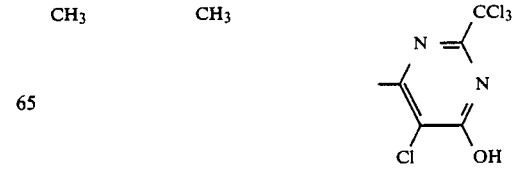 |

-continued
| | | |
|---|---|---|
| CH₃ | 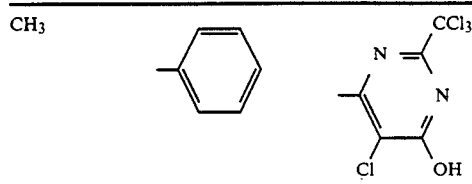 | 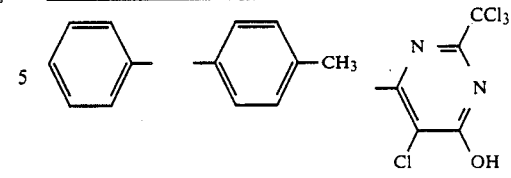 |
| CH₃ | 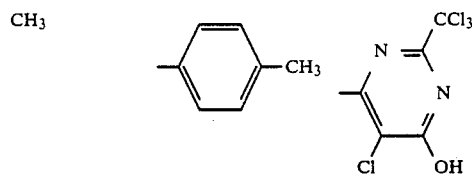 | 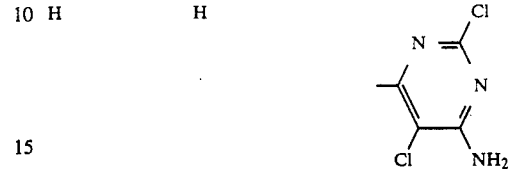 |
| CH₃O—CH₂— | H | 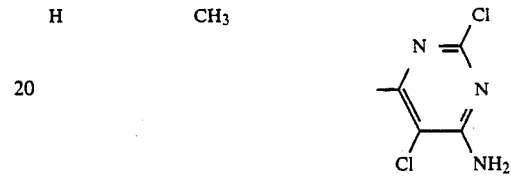 |
| CH₃O—CH₂— | CH₃ | 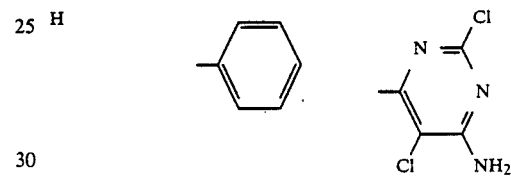 |
| CH₃O—CH₂— | 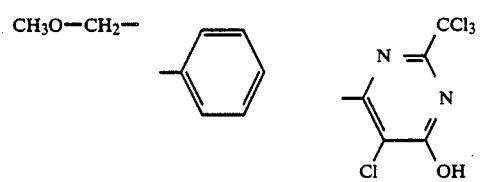 | 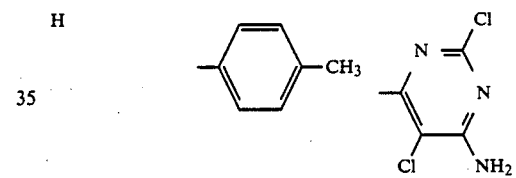 |
| CH₃O—CH₂— | 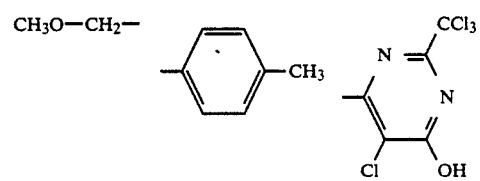 | 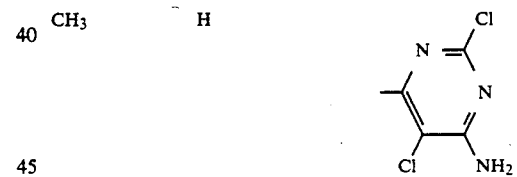 |
| 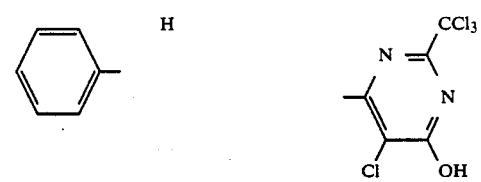 | H | 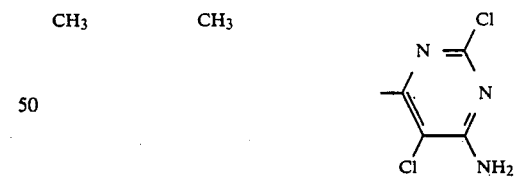 |
| 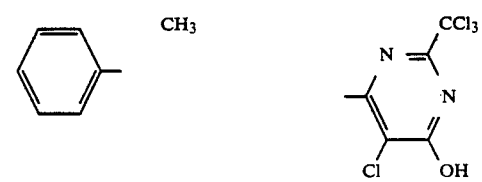 | CH₃ | 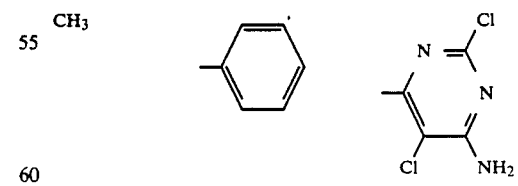 |
| 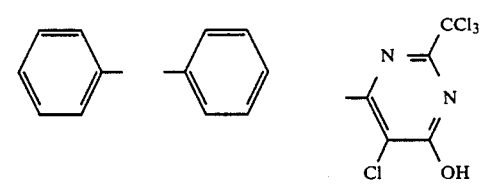 | | 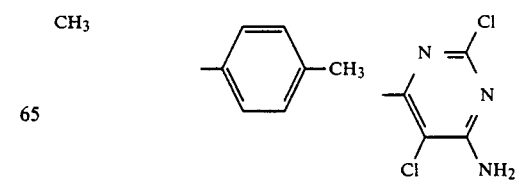 |
-continued
| | | |
|---|---|---|
| 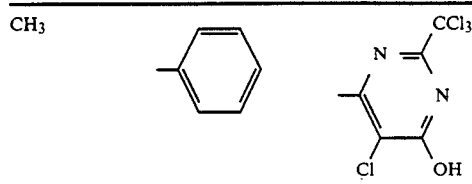 | 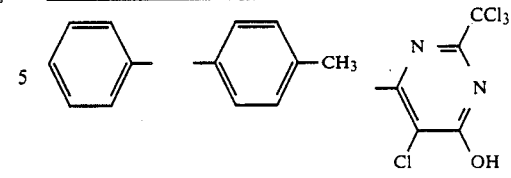 top | (see col 3 row 1) |
| H | H | |
| H | CH₃ | |
| H | (phenyl) | |
| H | (p-tolyl) | |
| CH₃ | H | |
| CH₃ | CH₃ | |
| CH₃ | (phenyl) | |
| CH₃ | (p-tolyl) | |

| | | |
|---|---|---|
| CH₃O—CH₂— | H | 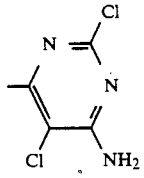 |
| CH₃O—CH₂— | CH₃ | 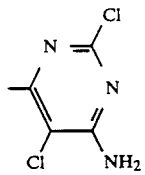 |
| CH₃O—CH₂— | 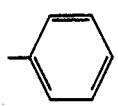 | 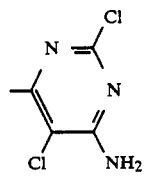 |
| CH₃O—CH₂— | 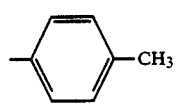 | 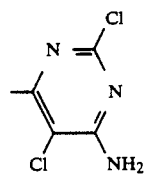 |
|  | H | 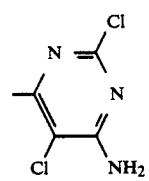 |
|  | CH₃ | 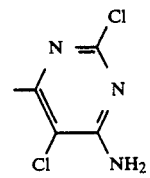 |
| 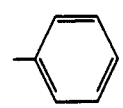 | 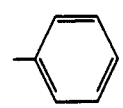 | 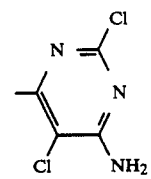 |
| 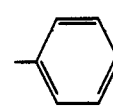 | 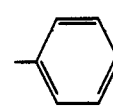 | 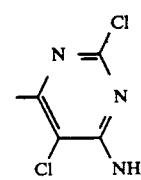 |
| H | H | 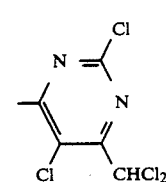 |
| | | |
|---|---|---|
| H | CH₃ | 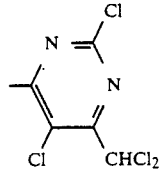 |
| 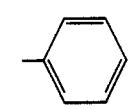 | | 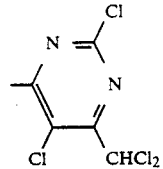 |
| H | 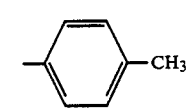 | 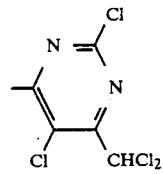 |
| CH₃ | H | 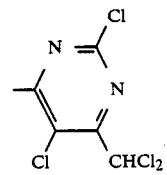 |
| CH₃ | CH₃ | |
| CH₃ | 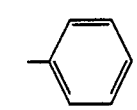 | 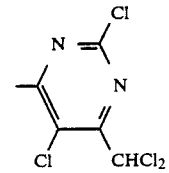 |
| CH₃ | 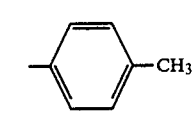 | 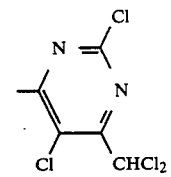 |
| CH₃O—CH₂— | H | 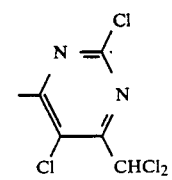 |
| CH₃O—CH₂— | CH₃ | 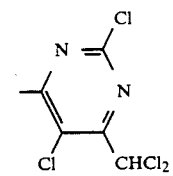 |

| | | |
|---|---|---|
| CH₃O—CH₂— | 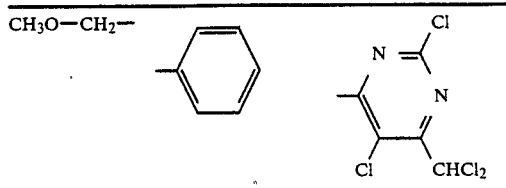 | |
| CH₃O—CH₂— | 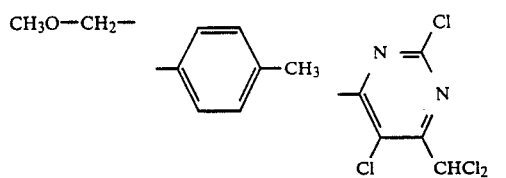 | |
| 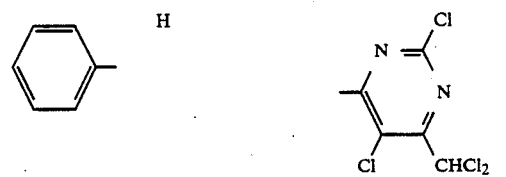 | H | |
| 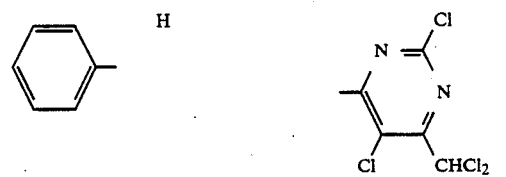 | CH₃ | |
| 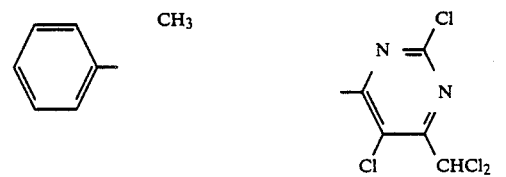 | 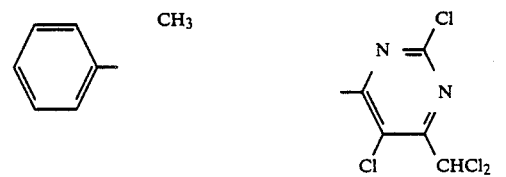 | |
| 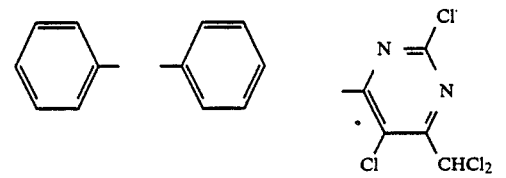 | 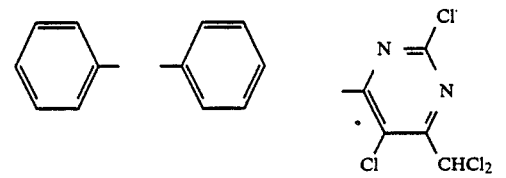 | |
| H | H | 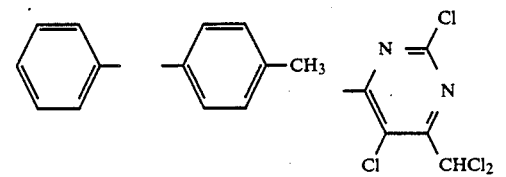 |
| H | CH₃ | 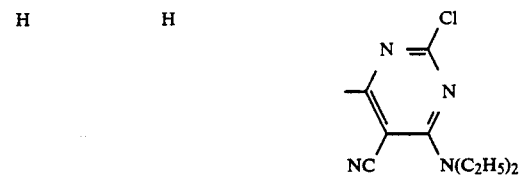 |
| H | 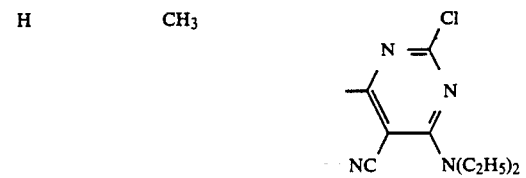 | 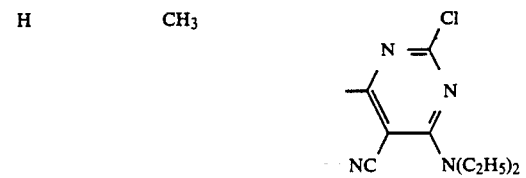 |
| | | |
|---|---|---|
| H | 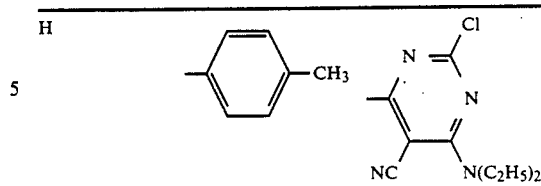 | |
| CH₃ | H | 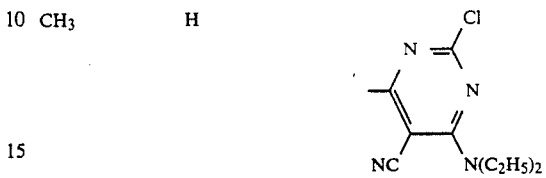 |
| CH₃ | CH₃ | 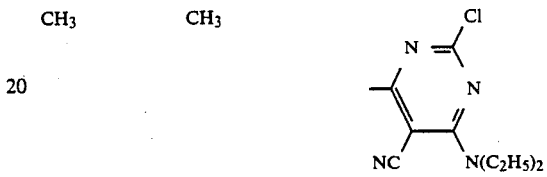 |
| CH₃ | 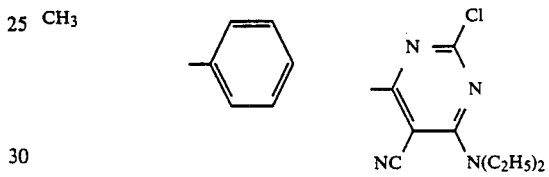 | 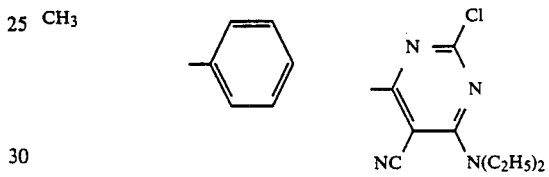 |
| CH₃ | 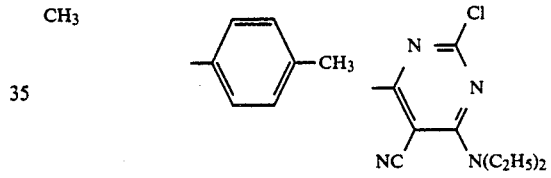 | |
| CH₃O—CH₂— | H | 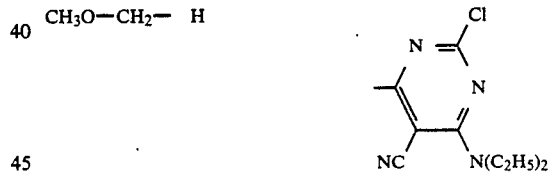 |
| CH₃O—CH₂— | CH₃ | 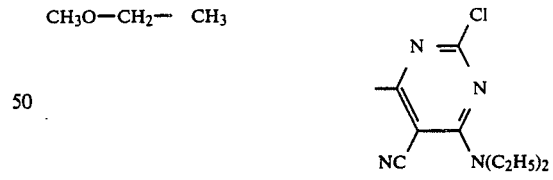 |
| CH₃O—CH₂— | 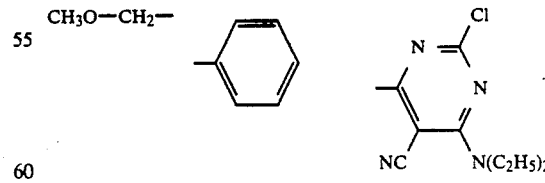 | 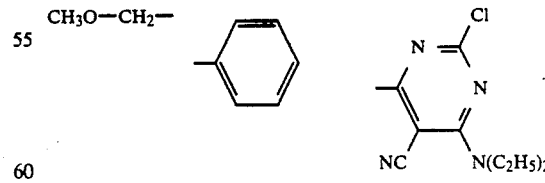 |
| CH₃O—CH₂— | 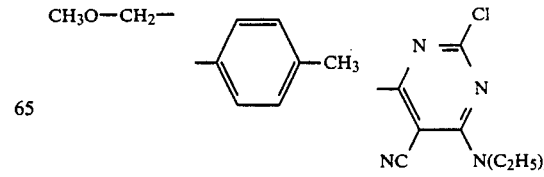 | |

| | | |
|---|---|---|
| 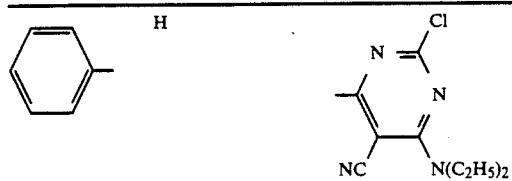 | H | 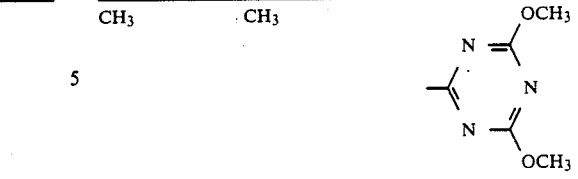 |
| 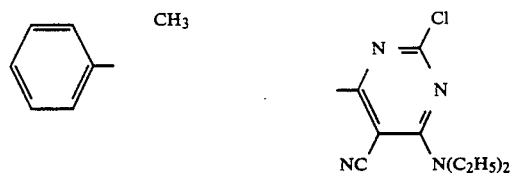 | CH₃ | 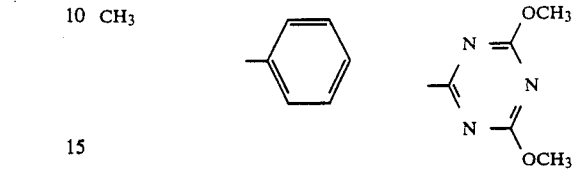 |
| 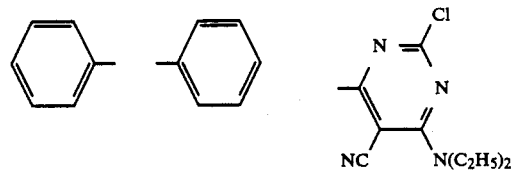 | 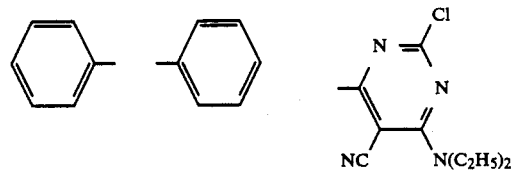 | 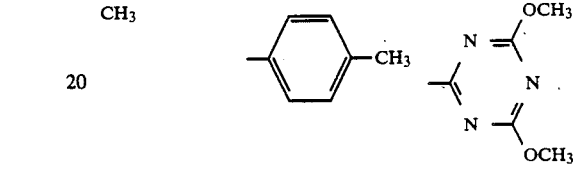 |
| 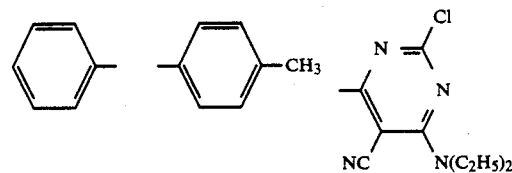 | 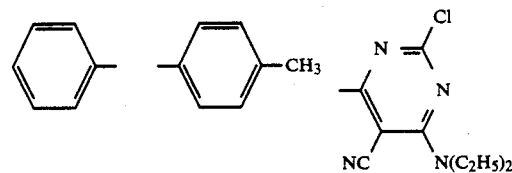 | 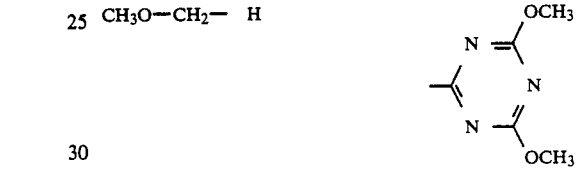 |
| H | H | 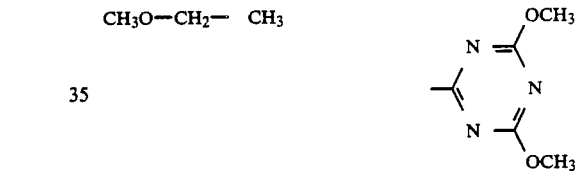 |
| H | CH₃ | 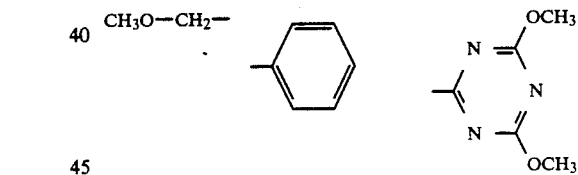 |
| H | 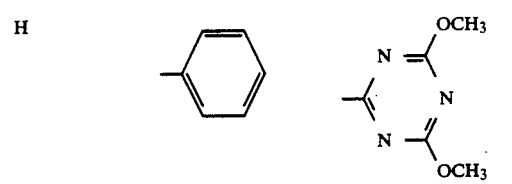 | 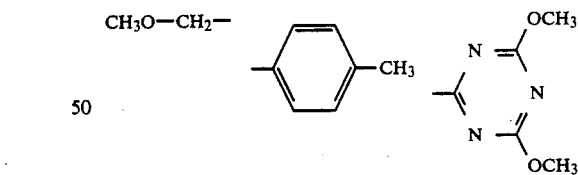 |
| H | 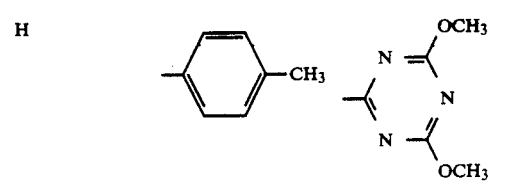 | 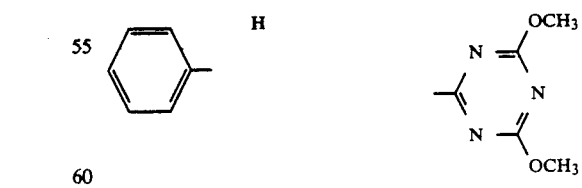 |
| CH₃ | H | 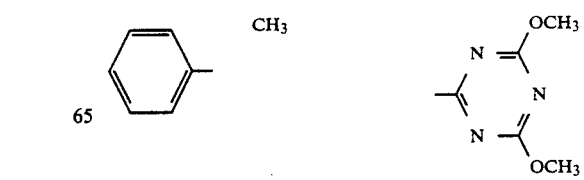 |
| | | |
|---|---|---|
| CH₃ | CH₃ | |
| CH₃ | 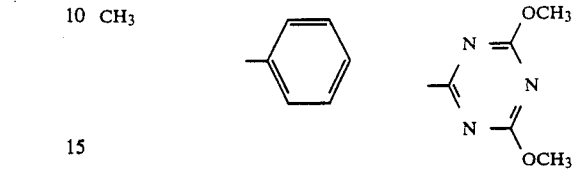 | |
| CH₃ | 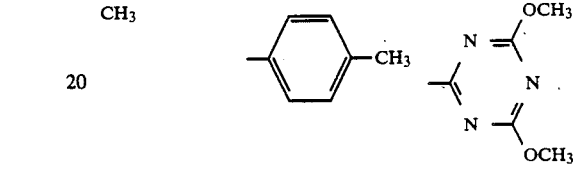 | |
| CH₃O—CH₂— | H | |
| CH₃O—CH₂— | CH₃ | |
| CH₃O—CH₂— | 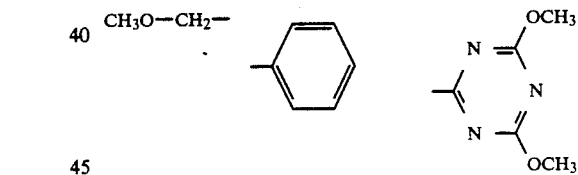 | |
| CH₃O—CH₂— | 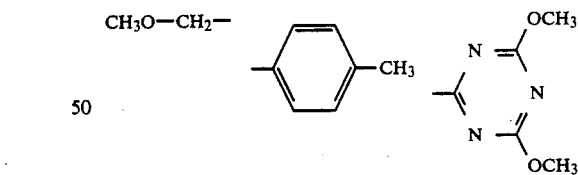 | |
| 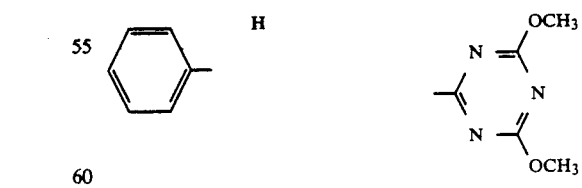 | H | |
| 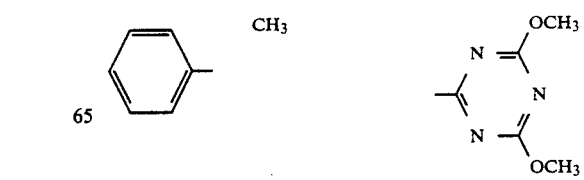 | CH₃ | |

| | | |
|---|---|---|
| 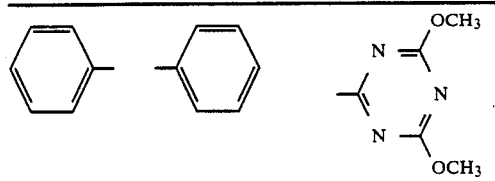 | | |
| 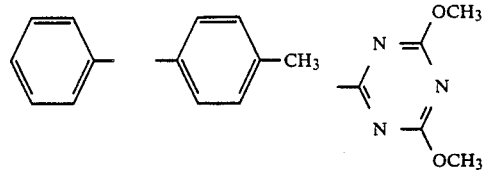 | | |
| H | H | 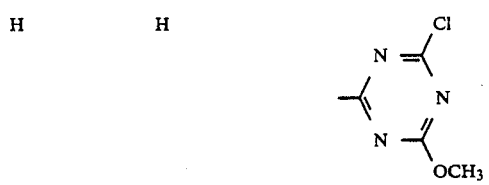 |
| H | CH₃ | 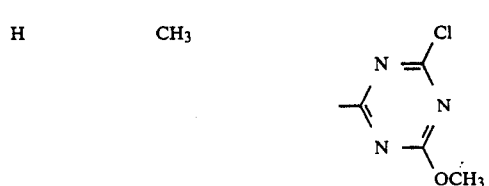 |
| H | | 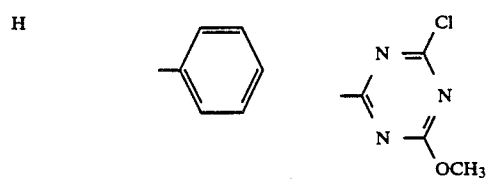 |
| H | | 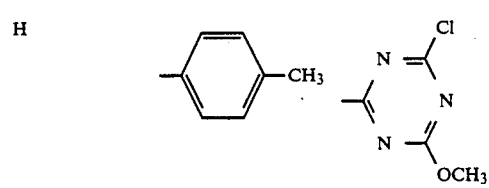 |
| CH₃ | H | 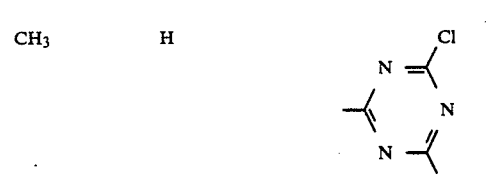 |
| CH₃ | CH₃ | 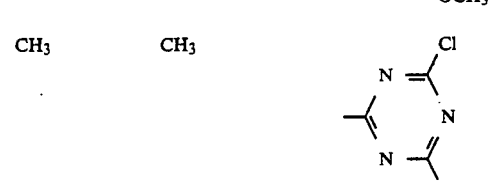 |
| CH₃ | | 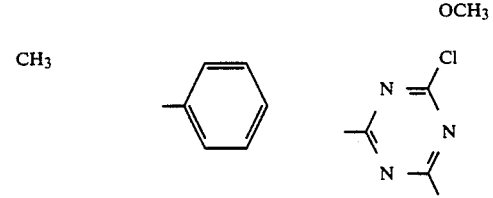 |
| | | |
|---|---|---|
| CH₃ | | 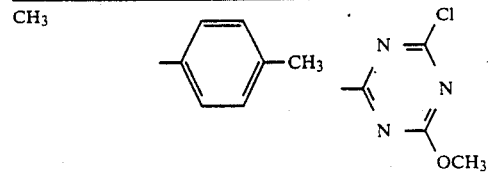 |
| CH₃O—CH₂— | H | 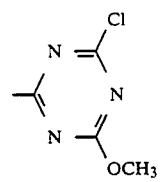 |
| CH₃O—CH₂— | CH₃ | 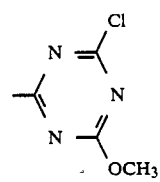 |
| CH₃O—CH₂— | | 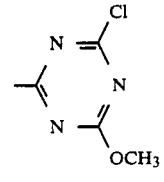 |
| CH₃O—CH₂— | | 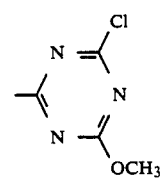 |
| | H | 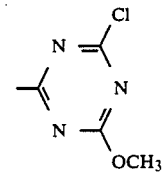 |
| | CH₃ | 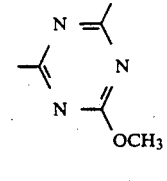 |
| | | 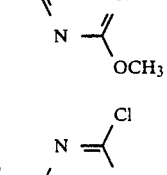 |
| | | 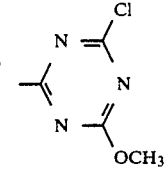 |

-continued
| | | |
|---|---|---|
| H | H | 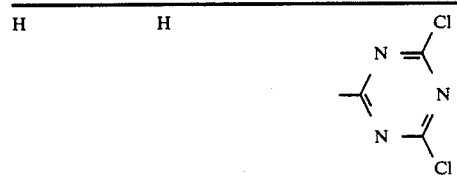 |
| H | CH₃ | 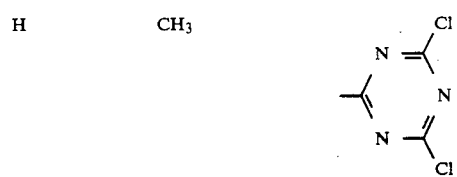 |
| H | 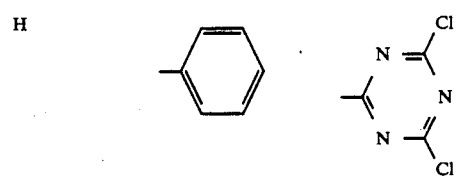 (phenyl) | 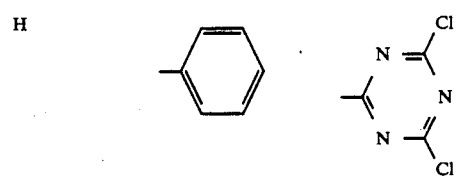 |
| H | 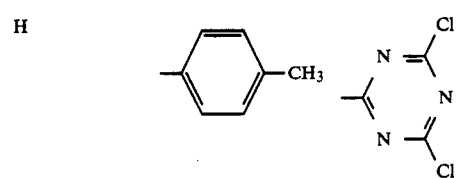 (p-tolyl) | 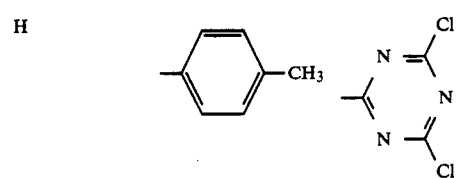 |
| CH₃ | H | 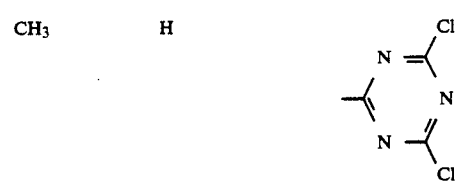 |
| CH₃ | CH₃ | 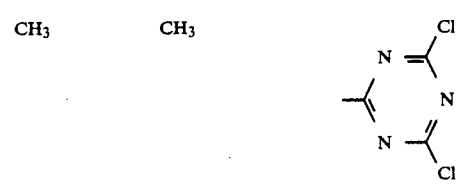 |
| CH₃ | 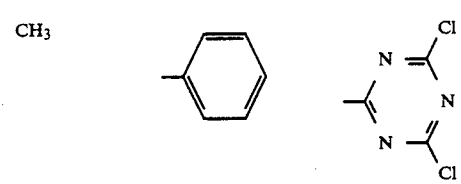 (phenyl) | 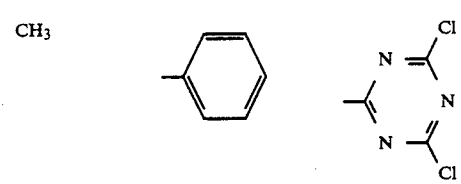 |
| CH₃ | 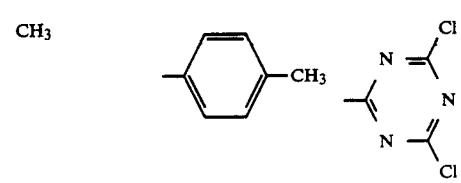 (p-tolyl) | 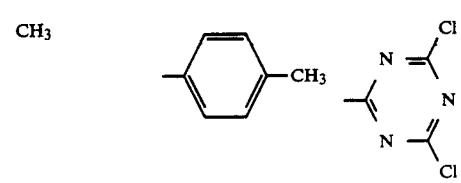 |
| CH₃O—CH₂— | H | 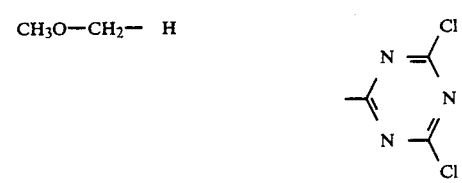 |
-continued
| | | |
|---|---|---|
| CH₃O—CH₂— | CH₃ | 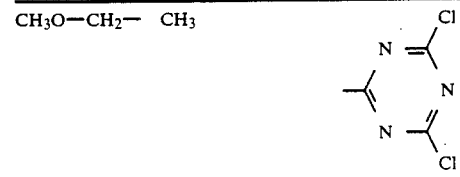 |
| CH₃O—CH₂— | (phenyl) | 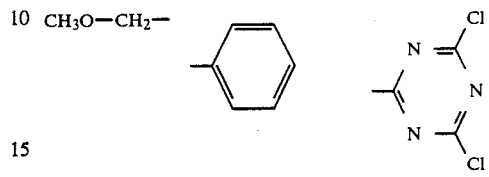 |
| CH₃O—CH₂— | (p-tolyl) | 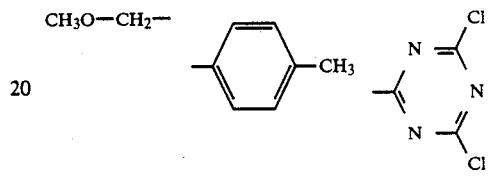 |
| (phenyl) | H | 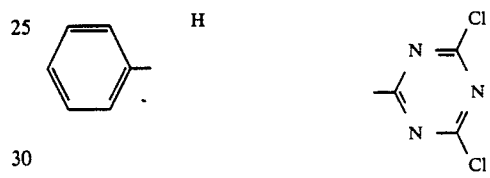 |
| (phenyl) | CH₃ | 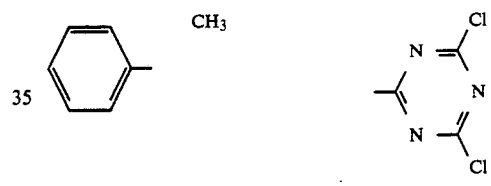 |
| (phenyl) | (phenyl) | 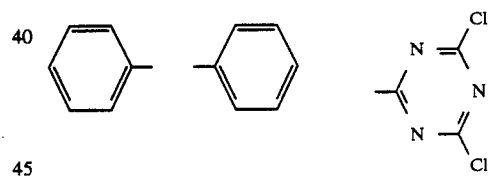 |
| (phenyl) | (p-tolyl) | 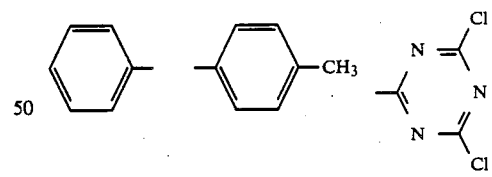 |
| H | H | 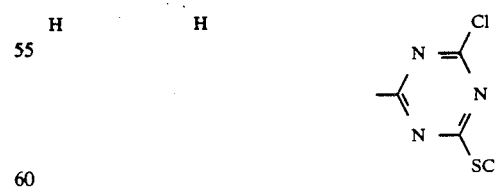 |
| H | CH₃ | 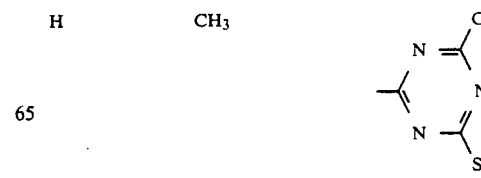 |

| | | |
|---|---|---|
| H | 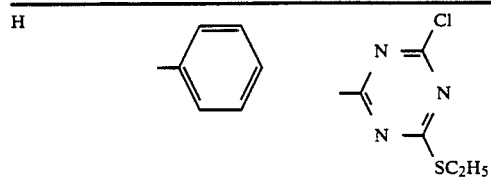 | |
| H | 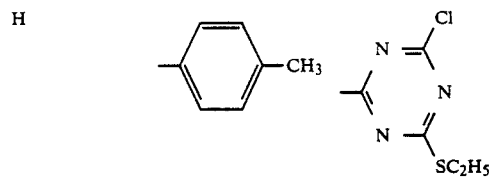 | |
| CH₃ | H | |
| CH₃ | CH₃ | |
| CH₃ | 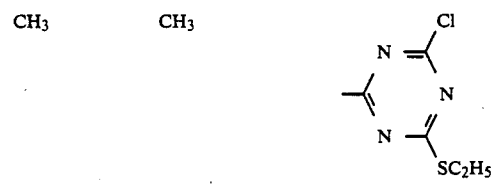 | |
| CH₃ | 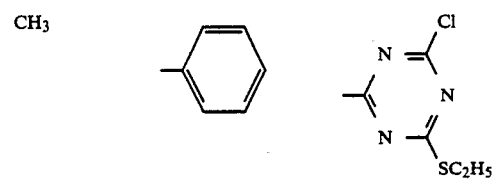 | |
| CH₃O—CH₂— | H | |
| CH₃O—CH₂— | CH₃ | |
| CH₃O—CH₂— | 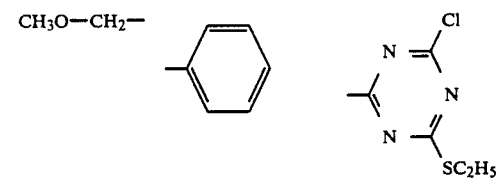 | |
| | | |
|---|---|---|
| CH₃O—CH₂— | 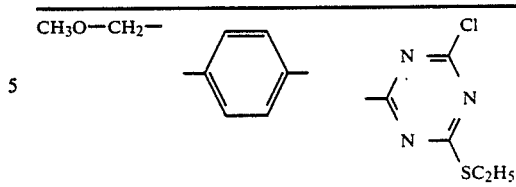 | |
| H | 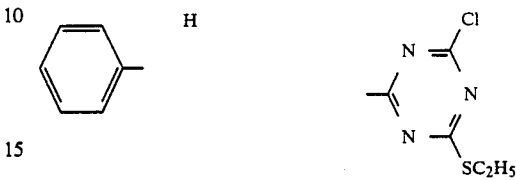 | |
| | CH₃ | |
| | 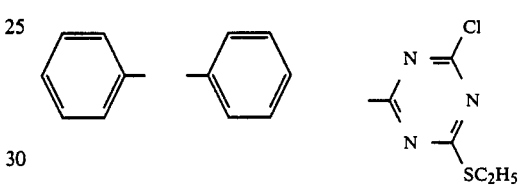 | |
| | 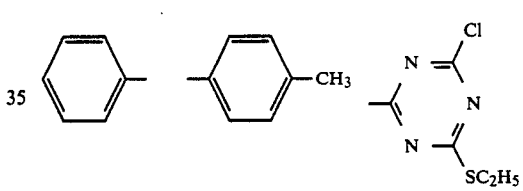 | |
| H | H | |
| H | CH₃ | |
| H | 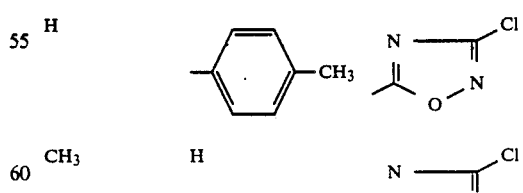 | |
| H | 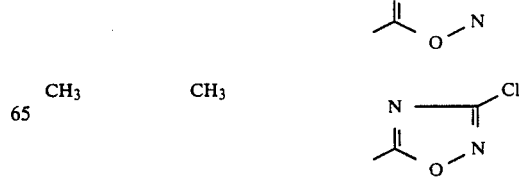 | |
| CH₃ | H | |
| CH₃ | CH₃ | |

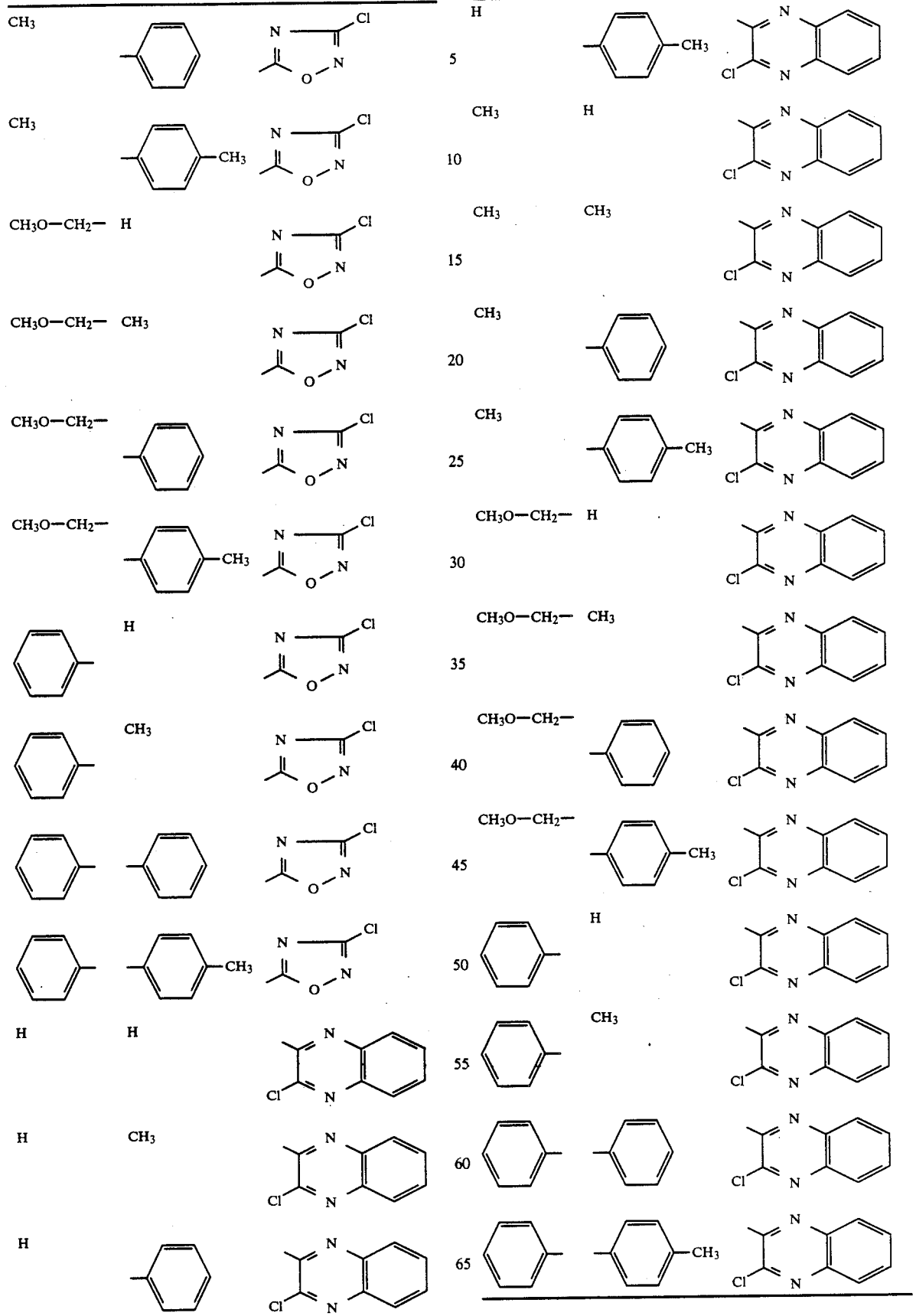

If, for example, 4-hydroximino-1,3-dimethylpyrazolin-5-one and 2,4,5,6-tetrachloropyrimidine are used as starting substances, the course of the reaction of process (a) according to the invention may be represented by the following equation:

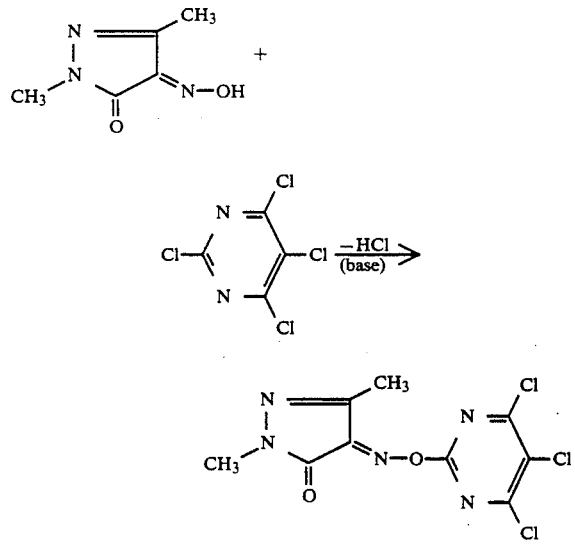

If, for example, ethyl β-keto-α-[(3-chloro-1,2,4-oxadiazol-5-yl)-oximino]-butyrate and phenylhydrazine are used as starting substances, the course of the reaction of process (b) according to the invention may be represented by the following equation:

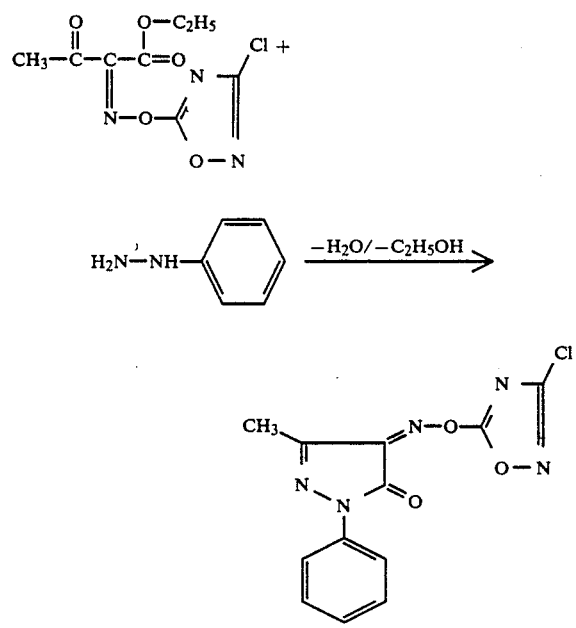

If, for example, 3-methyl-4-[(5-trifluoromethyl-pyrimidin-2-yl)-oximino]-pyrazolin-5-one and chloroacetonitrile are used as starting substances, the course of the reaction of process (c) according to the invention may be represented by the following equation:

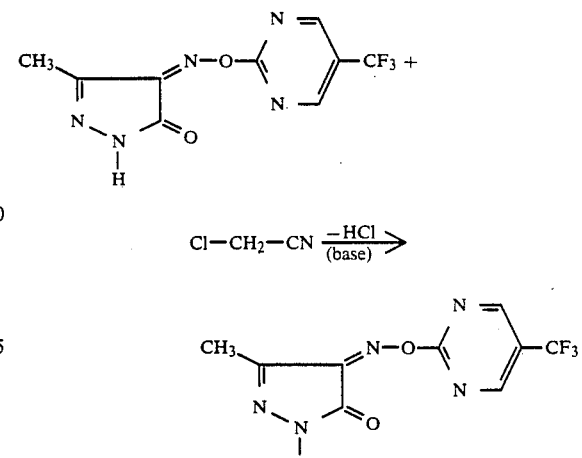

Formula (II) provides a general definition of the 4-oximino-pyrazolin-5-ones required as starting substances for carrying out process (a) according to the invention. In this formula (II), $R^1$ and $R^2$ preferably represent those radicals which have already been mentioned in the description of the substances of the formula (I) according to the invention as being preferred for these substituents. A preferably represents hydrogen or represents a sodium or potassium cation.

Some of the 4-oximino-pyrazolin-5-ones of the formula (II) are known [cf., for example, Ber. dtsch. chem. Ges. 29, 249 (1896); Coll. Czech. Chem. Commun. 25, 55 (1960); Arch. Pharm. 309, 900 (1976); Liebigs Ann. Chem. 1976, 1380].

They are obtained, for example, when β-ketoesters of the formula (VII)

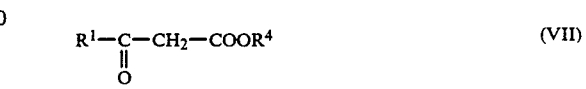

in which
$R^1$ has the abovementioned meaning and
$R^4$ represents lower alkyl, in particular methyl or ethyl, or when the ethoxymethylenemalonic ester of the formula (VIII)

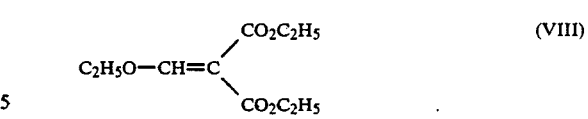

is initially cyclized in a 1st step with hydrazines of the formula (V)

in which
$R^2$ has the abovementioned meaning,
if appropriate in the presence of a diluent, such as, for example, ethanol, at temperatures between 0° C. and 100° C., the 4-ethoxycarbonylpyrazolin-5-ones of the formula (IX)

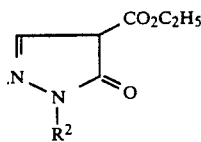 (IX)

in which
R² has the abovementioned meaning,
which result from the malonic ester of the formula (VIII) are hydrolyzed and decarboxylated in an intermediate step by customary methods, for example using aqueous hydrochloric acid, at temperatures between 50° C. and 120° C., and the resulting pyrazolin-5-ones of the formula (X)

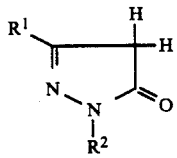 (X)

in which
R¹ and R² have the abovementioned meanings,
are reacted in a 2nd step (or 3rd step) with a nitrosylating agent, such as, for example, isopentyl nitrite or sodium nitrite, if appropriate in the presence of a diluent, such as, for example, ethanol, water or aqueous hydrochloric acid, and if appropriate in the presence of a base, such as, for example, sodium methoxide, at temperatures between −20° C. and +50° C.

Formula (III) provides a general definition of the heterocycles required as starting substances for carrying out process (a) according to the invention, In this formula (III), Het preferably represents those radicals which have already been mentioned in connection with the description of the substances of the formula (I) according to the invention as being preferred for these substituents. E¹ preferably represents halogen, in particular chlorine, bromine or iodine, or represents optionally substituted alkylsulphonyloxy, alkoxysulphonyloxy or arylsulphonyloxy, such as, for example, methanesulphonyloxy, methoxysulphonyloxy, trifluoromethanesulphonyloxy or p-toluenesulphonyloxy.

The heterocycles of the formula (III) are generally known compounds of organic chemistry. The β-ketoesters of the formula (VII) of the ethoxymethylenemalonic ester of the formula (VIII) are also generally known.

Formula (IV) provides a general definition of the alkoximinocarboxylic acid esters required as starting substances for carrying out process (b) according to the invention. In this formula (IV), R¹ and Het preferably represent those radicals which have already been mentioned in connection with the description of the substances of the formula (I) according to the invention as being preferred for these substituents. R preferably represents straight-chain or branched alkyl having 1 to 4 carbon atoms, in particular methyl or ethyl.

Some of the alkoximinocarboxylic acid esters of the formula (IV) are known (cf., for example, EP No. 210,815; JP No. 61/143,379; JP No. 61/171,464; JP No. 61/85,392; EP No. 147,181; EP No. 76,452 or J. Chem. Soc. Perkin Trans. I, 1984, 653–656).

They are obtained when hydroximinocarboxylic acid esters of the formula (XI)

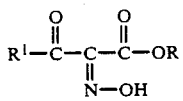 (XI)

in which
R and R¹ have the abovementioned meanings,
are reacted with heterocycles of the formula (III)

Het—E¹ (III)

in which
Het has the abovementioned meaning and
E1 represents an electron-withdrawing leaving group, in particular chlorine, bromine or iodine, or represents optionally substituted alkylsulphonyloxy, alkoxysulphonyloxy or arylsulphonyloxy, such as, for example, methanesulphonyloxy, methoxysulphonyloxy, trifluoromethanesulphonyloxy or p-toluenesulphonyloxy,
if appropriate in the presence of a diluent, such as, for example, acetonitrile, and if appropriate in the presence of an acid-binding agent, such as, for example, triethylamine, at temperature between +10° C. and +80° C.

The hydroximinocarboxylic acid esters of the formula (XI) are generally known compounds of organic chemistry (cf., for example, Helv. Chim. Acta 67, 906–915 [1984]; French patent application FR No. 2,434,572; Yakugaku Zasshi 87, 1209–1211 [1967] or Chem. Ber. 100, 1245–1247 [1967]).

Formula (Ia) provides a general definition of the 4-alkoximinopyrazolin-5-ones required as starting substances for carrying out process (c) according to the invention. In this formula (Ia), R¹ and Het preferably represent those radicals which have already been mentioned in connection with the description of the substances of the formula (I) according to the invention for these substituents.

The 4-alkoximinopyrazolin-5-ones of the formula (Ia) are compounds according to the invention and can be obtained with the aid of processes (a) or (b) according to the invention.

Formula (VI) provides a general definition of the alkylating agents furthermore required as starting substances for carrying out process (c) according to the invention.

In this formula (VI), R²' preferably represents those radicals which have already been mentioned in connection with the description of the substances of the formula (I) according to the invention for the substituent R², with the exception of the hydrogen radical and the unsubstituted or substituted aryl radicals. E² preferably represents those leaving groups which have already been mentioned in the description of the heterocycles of the formula (III) for the substituent E¹.

The alkylating agents of the formula (VI) are likewise generally known compounds or organic chemistry.

Suitable diluents for carrying out process (a) according to the invention are inert organic solvents or aqueous systems. These include, in particular, aliphatic or aromatic, optionally halogenated hydrocarbons, such as, for example, benzine, benzene, toluene, xylene, chlorobenzene, petroleum ether, hexane, cyclohexane, dichloromethane, chloroform, carbon tetrachloride; ethers, such as diethyl ether, dioxane, tetrahydrofuran or ethylene glycol dimethyl ether or ethylene glycol diethyl ether; ketones, such as acetone or butanone;

nitriles, such as acetonitrile or propionitrile; amides, such as dimethylformamide, dimethylacetamide, N-methylformanilide, N-methylpyrrolidone or hexamethylphosphoric triamide; esters, such as ethyl acetate; sulphoxides, such as dimethyl sulphoxide, and also water or aqueous/organic two-phase mixtures, such as dichloromethane/water or toluene/water.

If required, process (a) according to the invention is carried out in the presence of an acid-binding agent. Suitable acid-binding agents are all customary inorganic or organic bases. These include, for example, the hydroxides, amides, alkoxides or hydrides or alkali metals, such as sodium hydroxide or potassium hydroxide, sodium methoxide or potassium t-butoxide, sodium hydride or sodium amide; alkali metal carbonates, such as sodium carbonate, potassium carbonate or sodium hydrogencarbonate, and also tertiary amines, such as triethylamine, N,N-dimethylaniline,pyridine,N,N-dimethylaminopyridine, diazabicyclooctane (DABCO), diazabicyclononene (DBN) or diazabicycloundecene (DBU).

When carrying out process (a) according to the invention, the reaction temperature can be varied within a relatively wide range. In general, the process is carried out at temperature between $-20°$ C. and $+200°$ C. preferably at temperatures between $0°$ C. and $+150°$ C.

When carrying out process (a) according to the invention, 1.0 to 3.0 moles, preferably 1.0 to 1.5 moles, of heterocycle of the formula (III) and, if appropriate, 1.0 to 3.0 moles, preferably 1.0 to 1.5 moles, of acid-binding agent are generally employed per mole of 4-oximinopyrazolin-5-one of the formula (II).

If the reaction is carried out in an organic/aqueous two-phase system it is possible to carry out the reaction in the presence of 0.01 to 1 mole of a suitable phase-transfer catalyst, such as, for example, a quaternary ammonium or phosphonium compound. Triethylbenzylammonium chloride and benzyl-dodecyl-dimethylammonium chloride may be mentioned by way of example.

The reaction products of the formula (I) are worked up and isolated by customary methods.

Suitable diluents for carrying out process (b) according to the invention are likewise inert organic solvents. These include, in particular, aliphatic or aromatic, optionally halogenated hydrocarbons, such as, for example, benzine, benzene, toluene, xylene, chlorobenzene, petroleum ether, hexane, cyclohexane, dichloromethane, chloroform, carbon tetrachloride; ethers, such as diethyl ether, dioxane, tetrahydrofuran or ethylene glycol dimethyl ether or ethylene glycol diethyl ether, or alcohols, such as methanol, ethanol or propanol.

When carrying out process (b) according to the invention, the reaction temperatures can be varied within a relatively wide range. In general, the process is carried out at temperatures between $0°$ C. and $150°$ C., preferably at temperatures between $20°$ C. and $120°$ C.

For carrying out process (b) according to the invention, 0.8 to 2.5 moles, preferably 1.0 to 1.2 moles, of hydrazine derivative of the formula (V) are generally employed per mole of alkoximinocarboxylic acid ester of the formula (IV). The reaction is carried out and the reaction products of the formula (I) are worked up and isolated by customary methods.

Suitable diluents for carrying out process (c) according to the invention are likewise inert organic solvents or aqueous systems. The organic solvents indicated in process (a) or aqueous/organic two-phase mixtures are preferably used.

If appropriate, process (c) according to the invention is carried out in the presence of an acid-binding agent. Preferred acid-binding agents are those inorganic or organic bases which are indicated in process (a).

When carrying out process (c) according to the invetnion, the reaction temperatures can likewise be varied in a relatively wide range. In general, the process is carried out at temperatures between $-20°$ C. and $+200°$ C., preferably at temperatures between $0°$ C. and $+150°$ C.

When carrying out process (c) according to the invention, 1.0 to 3.0 moles, preferably 1.0 to 1.5 moles, of alkylating agent of the formula (VI) and, if appropriate, 0.5 to 3.0 moles, preferably 0.6 to 1.5 moles, of acid binding agent are generally employed per mole of 4-alkoximino-pyrazolin-5-one of the formula (Ia).

The reaction is carried out and the reaction products of the formula (I) are worked up and isolated as described in process (a), or by generally customary processes.

The active compounds according to the invention show a powerful action against pests and can be employed in practice for combating undesired pests. The active compounds are suitable for use as plant protection agents, in particular as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation:

Pythium species, such as, for example, *Pythium ultimum;*

Phytophthora species, such as, for example, *Phytophthora infestans;*

Pseudoperonospora species, such as, for example, *Pseudoperonospora humuli* or *Pseudoperonospora cubensis;*

Plasmopara species, such as, for example, *Plamopara viticola;*

Peronospora species, such as, for example, *Peronospora pisi* or *P. brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *P. graminea* (conidia form: Dreschslera, syn: Helminthosporium);

Cochliobolus species, such as, for example, *Cochliobolus sativus* (conida form: Dreschslera, syn: Helminthosporium);

Uromyces species, such as, for example, *Uromyces appendiculatus;*

Puccinia species, such as, for example, *Puccinia recondita;*

Tilletia species, such as, for example, *Tilletia caries;*

Ustilago species, such as, for example, *Ustilago nuda* or *Ustilago avenae;*

Pellicularia species, such as, for example, *Pellucularia sasakii;*

Pyricularia species, such as, for example, *Pyricularia oryzae;*
Fusarium species, such as, for example, *Fusarium culmorum;*
Botrytis species, such as, for example, *Botrytis cinerea;*
Septoria species, such as, for example, *Septoria nodorum;*
Leptosphaeria species, such as, for example, *Leptosphaeria nodorum;*
Cercospora species, such as, for example, *Cercospora canescens;*
Alternaria species, such as, for example, *Alternaria brassicae;*
Pseudocercosporella species, such as, for example, *Pseudocercosporella herpotrichoides.*

The good toleration, by plants, of the active compounds, at the concentrations required for combating plant diseases, permits treatment of above-ground parts of plants, or vegetative propagation stock and seeds, and of the soil.

Here, the active compounds according to the invention can be employed with particularly good success for combating rice diseases, such as, for example, against the organism causing rice blast disease (*Pyricularia oryzae*), or for combating diseases in fruit and vegetable growing, for example against the organism causing apple scab (*Venuria inaequalis*) or against Cercospora species. Besides a protective effectiveness, the active compounds according to the invention here also show systemic properties.

Depending on their particular physical and/or chemical properties, the active compounds can be converted to the customary formulations, such as solutions, emulsions, suspension, powders, foams, pastes, granules, aerosols, very fine capsules in polymeric substances and in coating compositions for seed, as well as ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinate aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water. By liquefied gaseous extenders or carriers are meant liquid which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly disperse silicic acid, alumina and silicates; as solid carriers for granules there are suitable: for example crushed and fractionated natural minerals such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable; for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysates. As dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations as a mixture with other known active compounds, such as fungicides, insecticides, acaricides and herbicides, as well as in mixtures with fertilizers and growth regulators.

The active compounds can be used as such or in the form of their formulations or the use forms prepared therefrom, such as ready-to-use solutions, suspensions, wettable powders, pastes, soluble powders, dusts and granules. They are used in the customary manner, for example by watering, spraying, atomizing, scattering, dusting, foaming, brushing on and the like. It is furthermore possible to apply the active compound formulation or the active compound itself into the soil. The seeds of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

In the treatment of soil, active compound concentrations of 0.00001 to 0.1% by weight, preferably 0.0001 to 0.02% by weight, are required at the place of action.

PREPARATION EXAMPLES

Example 1

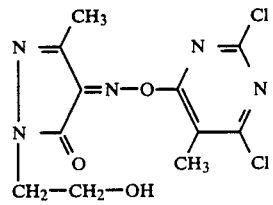

2.89 g (0.0344 mol) of sodium hydrogencarbonate and 10 ml of water are added to 2.94 g (0.0172 mol) of 1-(2- hydroxyethyl)-4-hydroximino-3-methylpyrazolin-5-one and 3.4 g (0.0172 mol) of 5-methyl-2,4,6-trichloropyrimidine (cf., for example, EP No. 126,711) in 100 ml of acetone, the mixture is stirred at room temperature for 15 hours and then concentrated in vacuo, the residue is taken up in dichloromethane, the mixture is washed with water, dried over sodium sulphate and concentrated again in vacuo, and the residue is purified by stirring with ethanol.

3.0 g (53% of theory) of 4-[(2,6-dichloro-5-methyl-pyrimidin-4-yl)-oximino]-1-(2-hydroxyethyl)-3-methyl-pyrazolin-5-one of melting point 120° C. are obtained.

PREPARATION OF THE STARTING COMPOUND

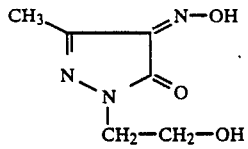

110.5 g (0.8 mol) of 1-(2-hydroxyethyl)-3-methyl-4H-pyrazolin-5-one in 600 ml of water are treated initially with 100 ml (1 mol) of concentrated hydrochloric acid and subsequently with 55.2 g (0.8 mol) of sodium nitrite in portions, with ice-cooling, and the mixture is stirred for 3 hours at room temperature after the addition is complete, and the precipitate formed is filtered off with suction, washed with water and dried.

122 g (89.2% of theory) or 4-hydroximino-1-(2-hydroxyethyl)-3-methyl-pyrazolin-5-one of melting point 166° C. are obtained.

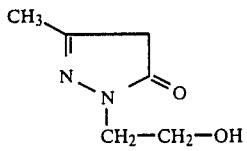

260 g (2 mol) of ethyl acetoacetate in 250 ml of ethanol are treated dropwise and with stirring with 152 g (2 mol) of 2-hydroxyethylhydrazine, during which process the temperature rises to 75° C. When the addition is complete, the mixture is stirred at room temperature for 15 hours and then concentrated in vacuo, and the oil which remains is crystallized by trituration with ether.

213 g (77% of theory) of 1-(2-hydroxyethyl)-3-methyl-4H-pyrazolin-5-one are obtained.

$^1$H-NMR (CDCl$_3$/tetramethylsilane): $\delta$=2.13 ppm.

The following substituted 4-heterocyclyloximino-pyrazolin-5-ones of the general formula (I) are obtained in a corresponding manner and in accordance with the general preparation instructions:

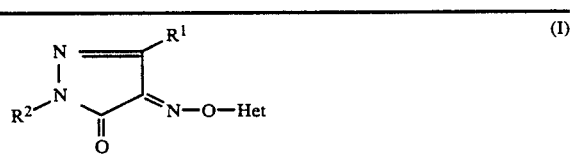

| Example No. | R$^1$ | R$^2$ | Het | Physical properties |
|---|---|---|---|---|
| 2 | H | CH$_3$ | ![structure with N, Cl, CH$_3$, Cl] | m.p. 161° C. |
| 3 | H | H | ![structure with N, Cl, CH$_3$, Cl] | m.p. 175–178° C. (dec.) |
| 4 | CH$_3$ | CH$_3$ | ![structure with N, Cl, CH$_3$, Cl] | m.p. 162–164° C. |
| 5 | CH$_3$ | CH$_3$ | ![structure with N, Cl, Cl] | m.p. 129–130° C. |

-continued

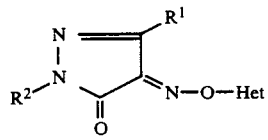
(I)

| Example No. | R¹ | R² | Het | Physical properties |
|---|---|---|---|---|
| 6 | CH₃ | CH₃ | 2-CCl₃-5,6-dichloropyrimidin-4-yl | m.p. 105–107° C. |
| 7 | CH₃ | 4-methylphenyl | 2,5,6-trichloropyrimidin-4-yl | m.p. 163–165° C. |
| 8 | CH₃ | phenyl | 2,5,6-trichloropyrimidin-4-yl | m.p. 163–165° C. |
| 9 | CH₃ | phenyl | 2-CCl₃-5,6-dichloropyrimidin-4-yl | m.p. 179–181° C. |
| 10 | CH₃ | 2-chlorophenyl | 2-CCl₃-5,6-dichloropyrimidin-4-yl | m.p. 178–181° C. |
| 11 | H | phenyl | 2-fluoro-5,6-dichloropyrimidin-4-yl | m.p. 164–166° C. |
| 12 | phenyl | CH₃ | 2-fluoro-5,6-dichloropyrimidin-4-yl | m.p. 153–155° C. |
| 13 | phenyl | CH₃ | 2-CCl₃-5,6-dichloropyrimidin-4-yl | m.p. 161–163° C. |

-continued
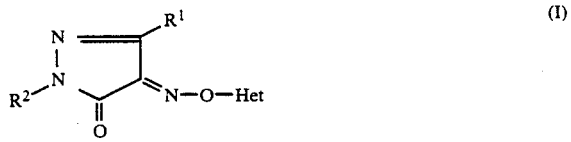
(I)
| Example No. | R¹ | R² | Het | Physical properties |
|---|---|---|---|---|
| 14 | $C_2H_5OOC-$ | $CH_3$ | 2-F, 5,6-diCl pyrimidin-4-yl | m.p. 148–151° C. |
| 15 | $C_2H_5OOC-$ | $CH_3$ | 2-$CCl_3$, 5,6-diCl pyrimidin-4-yl | m.p. 161–163° C. |
| 16 | $CH_3O-CH_2-$ | $CH_3$ | 2-F, 5,6-diCl pyrimidin-4-yl | m.p. 121–123° C. |
| 17 | $CH_3$ | p-tolyl | 2-$CCl_3$, 5,6-diCl pyrimidin-4-yl | m.p. 179–181° C. |
| 18 | $CH_3$ | p-tolyl | 2-F, 5-Cl, 6-$CHCl_2$ pyrimidin-4-yl | m.p. 173–175° C. |
| 19 | $CH_3$ | p-tolyl | 2-F, 5,6-diCl pyrimidin-4-yl | m.p. 163–165° C. |
| 20 | $CH_3$ | phenyl | 2-F, 5,6-diCl pyrimidin-4-yl | m.p. 163–165° C. |
| 21 | $CH_3$ | $CH_3$ | 2-F, 5,6-diCl pyrimidin-4-yl | m.p. 153–155° C. |

-continued
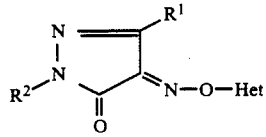
(I)
| Example No. | R¹ | R² | Het | Physical properties |
|---|---|---|---|---|
| 22 | CH₃ | CH₃ | 2-Cl, 4-Me, 6-Cl pyrimidin-5-yl with 3,4-dichlorophenyl | m.p. 210–211° C. |
| 23 | CH₃ | CH₃ | 2-Cl, 4-Me, 6-Cl pyrimidin-5-yl with 4-(CF₃)phenyl | m.p. 201–202° C. |
| 24 | CH₃ | CH₃ | 2-Cl, 4-Me, 6-Cl pyrimidin-5-yl with 3-(CF₃)phenyl | m.p. 143–145° C. |
| 25 | CH₃ | CH₃ | 2-Cl, 4-Me, 5-Br, 6-Cl pyrimidinyl | m.p. 154–155° C. |
| 26 | CH₃ | CH₃ | 2-Me, 5-F pyrimidinyl | m.p. 138–141° C. |
| 27 | CH₃ | phenyl | 3-Me, 5-CF₃ -1,2,4-thiadiazol-yl | m.p. 144° C. (dec.) |
| 28 | CH₃ | CH₃ | 3-Me, 5-CF₃ -1,2,4-thiadiazol-yl | m.p. 88° C. (dec.) |

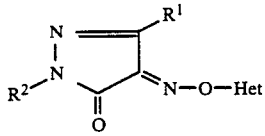

| Example No. | R[1] | R[2] | Het | Physical properties |
|---|---|---|---|---|
| 29 | H | CH₃ | 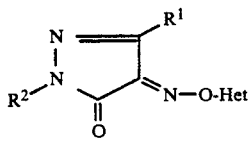 | m.p. 99° C. (dec.) |

Use Examples

In the following Use Examples, the compound listed below was employed as comparison substance:

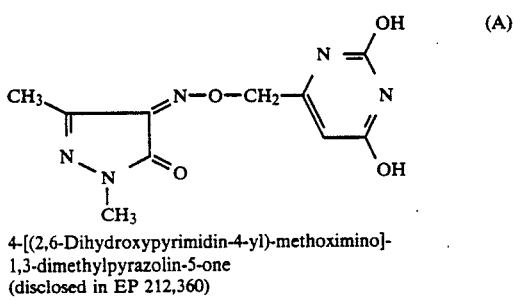

4-[(2,6-Dihydroxypyrimidin-4-yl)-methoximino]-1,3-dimethylpyrazolin-5-one
(disclosed in EP 212,360)

Example A

Pyricularia test (rice)/protective

Solvent: 12.5 parts by weight of acetone
Emulsifier: 0.3 part by weight of alkylaryl polyglycol ether To produce a suitable preparation of active compound, 1 part by weight of active compound is mixed with the stated amount of solvent, and the concentrate is diluted with water and the stated amount of emulsifier to the desired concentration.

To test for protective activity, young rice plants are sprayed with the preparation of active compound until dripping wet. After the spray coating has dried on, the plants are inoculated with an aqueous spore suspension of Pyricularia oryzae. The plants are then placed in a greenhouse at 100% relative atmospheric humidity and 25° C.

Evaluation of the disease infestation is carried out 4 days after the inoculation.

A clearly superior effectiveness compared with the prior art is shown in this test, for example, by the compounds according to Preparation Examples 1, 7, 8, 10, 11, 16, 19 and 20.

Example B

Pyricularia test (rice)/systemic

Solvent: 12.5 parts by weight of acetone
Emulsifier: 0.3 part by weight of alkylaryl polyglycol ether To produce a suitable preparation of active compound, 1 part by weight of active compound is mixed with the stated amount of solvent, and the concentrate is diluted with water and the stated amount of emulsifier to the desired concentration.

To test for systemic properties, standard soil in which young rice plants have been grown is watered with 40 ml of the preparation of active compound. 7 days after the treatment, the plants are inoculated with an aqueous spore suspension of Pyricularia oryzae. Thereafter, the plants remain in a greenhouse at a temperature of 25° C. and a relative atmospheric humidity of 100% until they are evaluated.

Evaluation of the disease infestation is carried out 4 days after the inoculation.

A clearly superior effectiveness compared with the prior art is shown in this test, for example, by the compounds according to Preparation Examples 7, 8, 10, 11, 16, 19 and 20.

It will be appreciated that the instant specification and claims are set forth by way of illustration and not limitation, and that various modifications and changes may be made without departing from the spirit and scope of the present invention.

What is claimed is:

1. A substituted 4-heterocyclyloximino-pyrazolin-5-one of the formula (I)

in which
R[1] and R[2] independently of one another in each case represent hydrogen, alkyl, alkenyl, alkinyl, cyanoalkyl, hydroxyalkyl, alkoxyalkyl, alkylthioalkyl, alcoxycarbonyl, hydroxycarbonylalkyl, alkoxycarbonylalkyl, aminocarbonylalkyl, alkylaminocarbonylalkyl or dialkylaminocarbonylalkyl, or represent in each case unsubstituted or in each case substituted oxiranylalkyl, aralkyl, heterocyclyl or aryl and Het represents an unsubstituted or substituted five-membered heterocycle.

2. A substituted 4-heterocyclyloximino-pyrazolin-5-one according to claim 1, in which
R[1] and R[2] independently of one another in each case represent hydrogen, in each case represent straight-chain or branched alkyl, alkenyl, alkinyl, cyanoalkyl, hydroxyalkyl, alkoxyalkyl, alkylthioalkyl, alkoxycarbonyl, hydroxycarbonylalkyl, alkoxycarbonylalkyl, aminocarbonylalkyl, alkylcarbonylalkyl or dialkylcarbonylalkyl, in each case having up to 8 carbon atoms in the individual alkyl or alkenyl or alkinyl moieties, or represent oxiranylalkyl having 1 to 4 carbon atoms in the straight-chain or branched alkyl moiety, or represent 1,1-dioxotetrahydrothienyl, or represent aralkyl which has 1 to 4 carbon atoms in the straight-chain or branched alkyl moiety and 6 to 10 carbon atoms in the aryl moiety and which is unsubstituted or monosubstituted to polysubstituted by identical or different substituents, or represent aryl which has 6 to 10 carbon atoms and which is unsubstituted or monosubstituted to polysubstituted by identical or different substituents, the substituents on the aryl moieties in each case being selected from the group consisting of halogen, cyano, nitro, hydroxyl, in each case straight-chain or branched alkyl, alkoxy, dioxyalkylene, alkylcarbonyloxy and alkylthio, in each case having up to 4 carbon atoms, in each case straight-chain or branched halogenoalkyl, halogenoalkoxy or halogenoalkylthio, in each case having 1 to 4 carbon atoms and 1 to 9 identical or different halogen atoms, and phenyl, and Het represents a saturated or unsaturated five-membered heterocycle which has 1 to 3 identical or different hetero atoms or hetero groupings and which is optionally benzo-fused and optionally substituted by substituents independently selected from the group consisting of hydroxyl, halogen, cyano, nitro, amino, in each case straight-chain or branched alkyl, alkoxy or alkylthio, in each case having 1 to 4 carbon atoms, in each case straight-chain or branched halogenoalkyl, halogenoalkoxy or halogenoalkylthio, in each case having 1 to 4 carbon atoms and 1 to 9 identical or different halogen atoms, in each case straight-chain or branched alkylamino, dialkylamino, alkoxycarbonyl or alkoximinoalkyl, in each case having 1 to 4 carbon atoms in the individual alkyl moieties, and phenyl which in turn is optionally substituted by substituents independently selected from the group consisting of nitro, halogen and in each case straight chain or branched or alkyl or alkoxy, in each case having 1 to 4 carbon atoms.

3. A substituted 4-heterocyclyloximino-pyrazolin-5-one according to claim 1, in which $R^1$ and $R^2$ independently of one another in each case represent hydrogen, methyl, ethyl, n- or i-propyl, ni, i-, s- or t-butyl, allyl butenyl, propargyl, cyanomethyl, cyanoethyl, hydroxymethyl, hydroxyethyl, methoxymethyl, methoxyethyl, ethoxymethyl, ethoxyethyl, methylthiomethyl, methoxycarbonyl, ethoxycarbonyl, hydroxycarbonylmethyl, hydroxycarbonylethyl, methoxycarbonylmethyl, methoxycarbonylethyl, ethoxycarbonylmethyl, ethoxycarbonylethyl, aminocarbonylmethyl, methylaminocarbonylmethyl, ethylaminocarbonylmethyl, dimethylaminocarbonylmethyl, diethylaminocarbonylmethyl, aminocarbonylethyl, oxiranylmethyl, oxiranylethyl, or represent 1,1-dioxotetrahydrothien-3-yl, or represent phenyl or benzyl which are unsubstituted or in each case monosubstituted to trisubstituted on the phenyl by substituents independently selected from the group consisting of fluorine, chlorine, bromine, iodine, cyano, nitro, hydroxyl, methyl, ethyl, n- or i-propyl, n-, i-, s- or ti-butyl, methoxy, ethoxy, dioxymethylene, dioxyethylene, methylthio, ethylthio, acetoxy or propionyloxy, chloromethyl, dichloromethyl, trichloromethyl, trifluoromethyl, dichlorofluoromethyl, chlorodifluoromethyl, trifluoromethoxy, trifluoromethylthio and phenyl and Het represents a heterocycle which is bonded via a carbon atom, of the formula

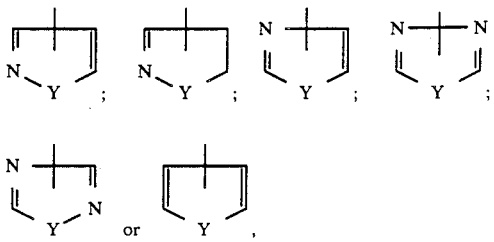

and which is optionally benzo-fused and which is optionally substituted up to three times by substituents independently selected from the group consisting of hydroxyl, amino, cyano, nitro, fluorine, chlorine, bromine, methyl, ethyl, n- or i-propyl, n-, i- s- or t-butyl, methoxy, ethoxy, methylthio, ethylthio, trifluoromethyl, trichloromethyl, dichloromethyl, chloromethyl, difluoromethyl, fluoromethyl, trifluoromethoxy, difluoromethoxy, trifluoromethylthio, methylamino, ethylamino, dimethylamino, diethylamino, methoxycarbonyl, ethoxycarbonyl, methoximinomethyl, ethoximinomethyl, methoximinoethyl or ethoximinoethyl, and phenyl which is unsubstituted or monosubstituted to trisubstituted by identical or different substituents from the group consisting of chlorine, nitro, methyl, ethyl and methoxy, and Y represents oxygen, sulphur, sulphinyl or sulphonyl.

4. A substituted 4-heterocyclyloximino-pyrazolin-5-one according to claim 1, in which $R^1$ and $R^2$ independently of one another in each case represent hydrogen, methyl, ethyl, n- or i-propyl, or represent methoxymethyl, or represent hydroxyethyl, or represent methoxycarbonyl or ethoxycarbonyl, or represent phenyl which is unsubstituted or monosubstituted or disubstituted by identical or different substituents from the group consisting of chlorine, nitro, methyl, ethyl and methoxy.

5. A compound according to claim 1, wherein such compound is 4-[(5-trifluoromethyl-1,3,4-thiadiazol-2-yl)-oximino]-1-phenyl-3-methylpyrazolin-5-one, of the formula

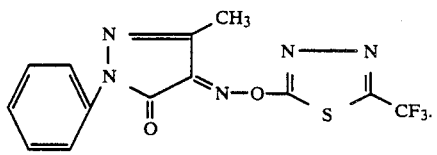

6. A compound according to claim 1, wherein such compound is 4-[(5-trifluoromethyl-1,3,4-thiadiazol-2-yl)-oximino]-1,3, dimethyl-pyrazolin-5-one, of the formula

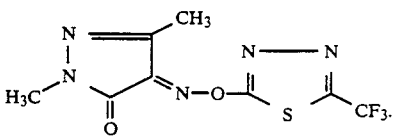

7. A compound according to claim 1, wherein such compound is 4-[(5-trifluoromethyl-1,3,4-thiadiazol-2-yl)-oximino]-1-methyl-pyrazolin-5-one, of the formula

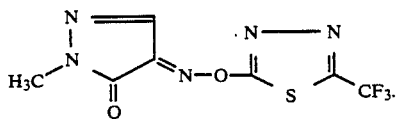

8. A fungicidal composition comprising a fungicidally effective amount of a compound according to claim 1 and a diluent.

9. A method of combatting fungi which comprises applying to such fungi or to a fungus habitat a fungicidally effective amount of a compound according to claim 1.

10. The method according to claim 9, wherein in such compound is

4-[(5-trifluoromethyl-1,3,4-thiadiazol-2-yl)-oximino]-1phenyl-3-methylpyrazolin-5-one, 4-[(5-trifluoromethyl-1,3,4-thiadiazol-2-yl)-oximino]-1,3, dimethyl-pyrazolin-5-one or 4-[(5-trifluoromethyl-1,3,4-thiadiazol-2-yl)-oximino]-1-methyl-pyrazolin-5-one.

* * * * *